(12) United States Patent
Yamaguchi et al.

(10) Patent No.: US 7,776,849 B2
(45) Date of Patent: Aug. 17, 2010

(54) BENZENOID ANSAMYCIN DERIVATIVE

(75) Inventors: Shinpei Yamaguchi, Sunto-gun (JP); Takayuki Nakashima, Sunto-gun (JP); Yutaka Kanda, Machida (JP)

(73) Assignee: Kyowa Hakko Kirin Co., Ltd., Tokyo (JP)

( * ) Notice: Subject to any disclaimer, the term of this patent is extended or adjusted under 35 U.S.C. 154(b) by 288 days.

(21) Appl. No.: 11/917,239

(22) PCT Filed: Jun. 29, 2006

(86) PCT No.: PCT/JP2006/312992
§ 371 (c)(1),
(2), (4) Date: Dec. 12, 2007

(87) PCT Pub. No.: WO2007/001049
PCT Pub. Date: Jan. 4, 2007

(65) Prior Publication Data
US 2009/0048253 A1    Feb. 19, 2009

(30) Foreign Application Priority Data
Jun. 29, 2005    (JP)    ............... 2005-190493

(51) Int. Cl.
*A61K 31/395*    (2006.01)
*C07D 225/06*    (2006.01)
*A61P 35/00*    (2006.01)
(52) U.S. Cl. ..................... 514/183; 540/461
(58) Field of Classification Search ................. 540/461; 514/183
See application file for complete search history.

(56) References Cited

U.S. PATENT DOCUMENTS

| | | |
|---|---|---|
| 6,946,456 B2 | 9/2005 | Rosen et al. |
| 7,241,754 B2 | 7/2007 | Tian et al. |
| 2005/0026894 A1 | 2/2005 | Tian et al. |
| 2009/0209507 A1 | 8/2009 | Gaisser et al. |

FOREIGN PATENT DOCUMENTS

| | | |
|---|---|---|
| JP | 57-163369 | 10/1982 |
| JP | 64-009976 | 1/1989 |
| JP | 01-175970 | 7/1989 |
| JP | 8-502488 | 3/1996 |
| JP | 09-286779 | 11/1997 |
| JP | 2004-505044 | 2/2004 |
| WO | 94/08578 | 4/1994 |
| WO | 02/069900 | 9/2002 |
| WO | 2005/061461 | 7/2005 |

OTHER PUBLICATIONS

Rinehart, "Geldanamycin. I: Structure Assignment", Journal of the American Chemical Society, vol. 92, No. 26 (1970) 7591-93.

Ko, et al., "Model studies for the total synthesis of the Maytansinoids based . . . ", Tetrahedron, vol. 41, No. 17 (1985) 3511-18.

Lemarchand, et al., "Synthesis of a para-quinone macrolactam related to . . . ", Tetrahedron, vol. 60, No. 43 (2004) 9659-73.

Patel, et al., "Engineered Biosynthesis of Geldanamycin Analogs for Hsp90 Inhibition", Chemistry & Biology, vol. 11, No. 12 (2004) 1625-33.

Andrus, et al., "Total Synthesis of (+)-Geldanamycin and (−)-o-Quinogeldanamycin: Asymmetric Glycolate Aldol Reactions and Biological Evaluation", J. Org. Chem., vol. 68 (2003) 8162-69.

Chiosis, et al., "A small moleculre designed to bind the adenine nucleotide pocket of Hsp90 causes Her2 degradation and the growth arrest and differentiation of breast cancer cells", Chemistry & Biology, vol. 8 (2001) 289-99.

Li, et al., "Isolation and Structure Elucidation of Autolytimycin, A New Compound Produced by *Streptomyces autolyticus* JX-47", Chinese Chemical Letters, vol. 12, No. 10 (2001) 903-06.

Marcu, et al., "Novobiocin and Related Coumarins and Depletion of Heat Shock Protein 90-Dependent Signaling Proteins", Journal of the National Cancer Institute, vol. 92, No. 3 (2000) 242-48.

(Continued)

*Primary Examiner*—Bruck Kifle
(74) *Attorney, Agent, or Firm*—Fitzpatrick, Cella, Harper & Scinto

(57) ABSTRACT

The present invention provides a benzenoid ansamycin derivative represented by Formula (I)

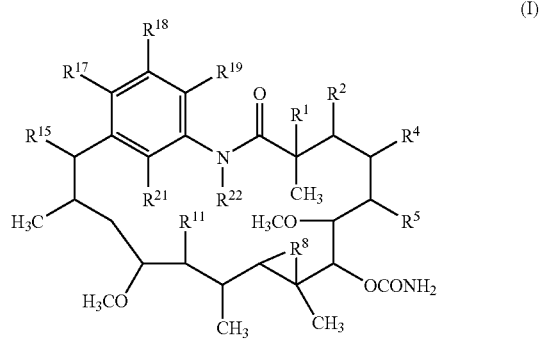

(wherein $R^1$ and $R^2$ each represent a hydrogen atom or are combined together to form a bond,
$R^8$ represents a bond or an oxygen atom,
$R^{11}$ represents hydroxy, substituted or unsubstituted lower alkoxy or substituted or unsubstituted lower alkanoyloxy,
$R^{15}$ represents a hydrogen atom or methoxy,
$R^{22}$ represents a hydrogen atom, substituted or unsubstituted lower alkyl, substituted or unsubstituted lower alkanoyl or substituted or unsubstituted aroyl,
$R^4$ and $R^5$ each represent a hydrogen atom or are combined together to form a bond,
$R^{18}$ represents a hydrogen atom, or the like,
$R^{21}$ represents hydroxy or the like, and
$R^{17}$ and $R^{19}$ may be the same or different and each represents a hydrogen atom, or the like) or a pharmaceutically acceptable salt thereof.

20 Claims, No Drawings

OTHER PUBLICATIONS

Nakata, et al., "Total Synthesis of Herbimycin A", Tetrahedron Letters, vol. 32, No. 42 (1991) 6015-18.

Neckers, et al., "Geldanamycin as a potential anti-cancer agent: Its molecular target and biochemical activity", Investigational New Drugs, vol. 17 (1999) 361-73.

Roe, et al., "Structural Basis for Inhibition of the Hsp90 Molecular Chaperone by the Antitumor Antibiotics Radicicol and Geldanamycin" J. Med. Chem., vol. 42 (1999) 260-66.

Schnur, et al., "Inhibition of the Oncogene Product p185erbB-2 in Vitro and in Vivo by Geldanamycin and Dihydrogeldanamycin Derivatives", J. Med. Chem., vol. 38 (1995) 3806-12.

Schulte, et al., "Antibiotic radicicol binds to the N-terminal domain of Hsp90 and shares important biologic activities with geldanamycin", Cell Stress & Chaperones, vol. 3, No. 2 (1998) 100-08.

Shiotsu, et al., "Novel oxime derivatives of radicicol induce erythroid differentiation associated with preferential G 1 phase accumulation against chronic . . . ", Blood, vol. 96, No. 6 (2000) 2284-91.

Soga, et al., "KF25706, a Novel Oxime Derivative of Radicicol, Exhibits in Vivo Antitumor Activity via Selective Depletion of Hsp90 Binding Signaling Molecules", Cancer Research, vol. 59 (1999) 2931-38.

Soga, et al., "Stereospecific antitumor activity of radicicol oxime derivatives", Cancer Chemother Pharmacol, vol. 48 (2001) 435-45.

Stead, et al., "Discovery of Novel Ansamycins Possessing Potent Inhibitory Activity in a Cell-based Oncostatin M Signalling Assay", The Journal of Antibiotics, vol. 53, No. 7 (2000) 657-63.

Takatsu, et al., "Reblastatin, a Novel Benzenoid Ansamycin-type Cell Cycle Inhibitor", The Journal of Antibiotics, vol. 53, No. 11 (2000) 1310-12.

BENZENOID ANSAMYCIN DERIVATIVE

TECHNICAL FIELD

The present invention relates to heat shock protein 90 (Hsp90) family protein inhibitors useful for a pharmaceutical such as an antitumor agent, an angiogenic inhibitor, or the like, and benzenoid ansamycin derivatives.

BACKGROUND ART

Known examples of Hsp90 family proteins include Hsp90α proteins, Hsp90β proteins, grp94, and Hsp75/TRAP1 ("Pharmacology & Therapeutics", 1998, vol. 79, p. 129-168, and "Molecular Endocrinology", 1999, vol. 13, p. 1435-1448).

Hitherto, benzoquinone ansamycin antibiotics, such as Geldanamycin and Herbimycin, and Radicicol are known as compounds that bind to Hsp90 family proteins (for example, see Non-Patent Documents 1 and 2). It is reported that these compounds all bind to Hsp90 family proteins and inhibit the functions of Hsp90 family proteins, thereby exhibiting pharmacological activities such as anti-tumor activity. Therefore, compounds that bind to Hsp90 family proteins are possibly useful as therapeutic agents for diseases associated with Hsp90 family proteins or proteins to which Hsp90 family proteins are bound (Hsp90 client proteins).

Geldanamycin derivatives (for example, see Non-Patent Document 3) and Radicicol derivatives (for example, see Non-Patent Documents 4 to 6) are reported to exhibit antitumor effects.

Novobiocin and PU3 are reported to bind to Hsp90 family proteins (for example, see Non-Patent Document 7 and 8).

Reblastatin, Autolytimycin, and 17-O-Demethylreblastatin are known as benzenoid ansamycin derivatives. Reblastatin is reported to inhibit retinoblastoma (Rb) protein phosphorylation to arrest the cell cycle at the G1 phase (for example, see Patent Document 1 and Non-Patent Document 9). Autolytimycin and 17-O-Demethylreblastatin are reported as anti-HSV-1 agents (for example, Non-Patent Document 10) and Oncostatin M inhibitors (for example, see Non-Patent Document 11). Furthermore, Compound A and derivatives thereof are reported to exhibit Hsp90 inhibitory activity and cytostatic activity (see Patent Document 2). Compound B (see Non-Patent Document 12) and Compound C (see Patent Document 3) are known. Furthermore, Compound D (see Non-Patent Document 13) and Compound E (see Non-Patent Document 14) are known.

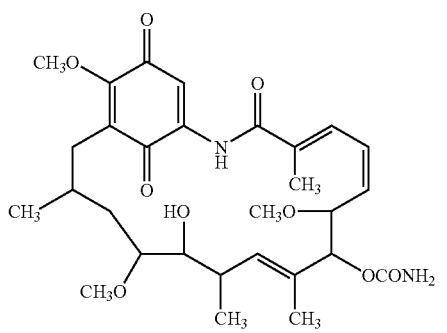

Geldanamycin

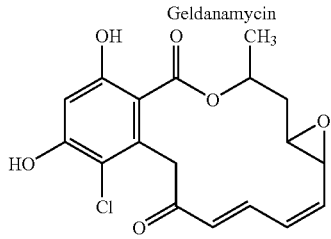

Radicicol

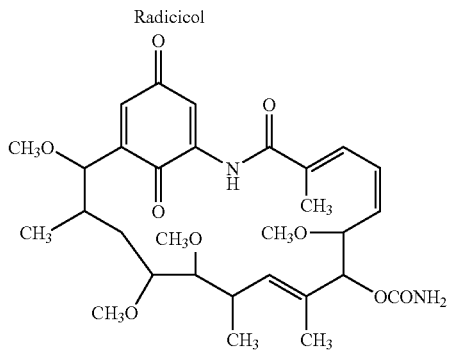

HerbimycinA

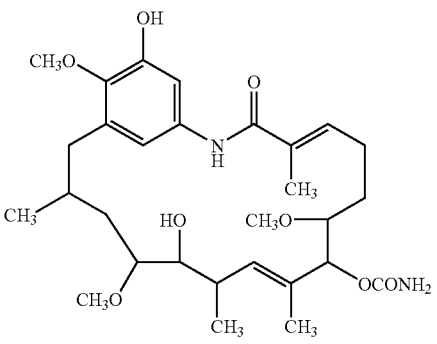

Reblastatin

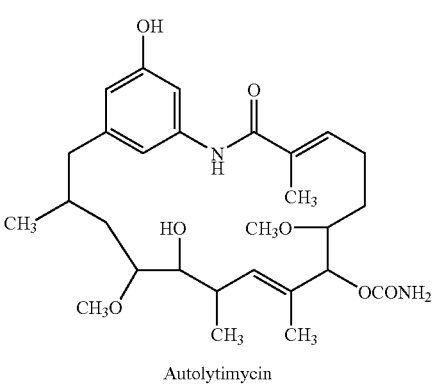

Autolytimycin

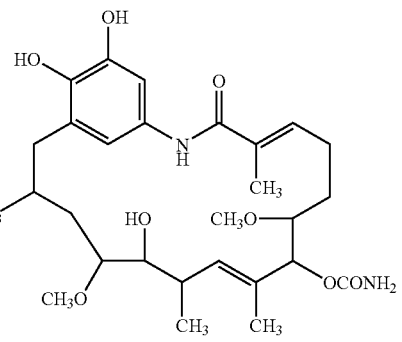

17-O-Demethylreblastatin

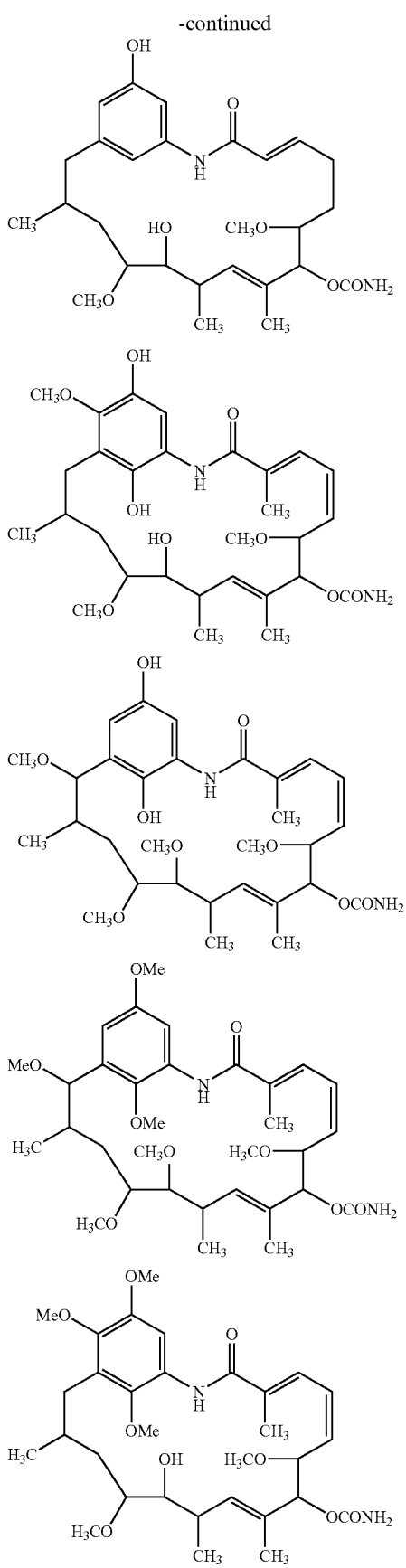

[Patent Document 1] Japanese Unexamined Patent Application Publication No. 9-286779
[Patent Document 2] U.S. Published Application No. 2005/0026894
[Patent Document 3] Japanese Unexamined Patent Application Publication No. 1-175970
[Non-Patent Document 1] "Cell Stress & Chaperones", 1998, vol. 3, p. 100-108
[Non-Patent Document 2] "Journal of Medicinal Chemistry", 1999, vol. 42, p. 260-266
[Non-Patent Document 3] "Investigational New Drugs", 1999, vol. 17, p. 361-373
[Non-Patent Document 4] "Cancer Research", 1999, vol. 59, p. 2931-2938
[Non-Patent Document 5] "Blood", 2000, vol. 96, p. 2284-2291
[Non-Patent Document 6] "Cancer Chemotherapy and Pharmacology", 2001, vol. 48, p. 435-445
[Non-Patent Document 7] "Journal of National Cancer Institute", 2000, vol. 92, p. 242-248
[Non-Patent Document 8] "Chemistry & Biology", 2001, vol. 8, p. 289-299
[Non-Patent Document 9] "Journal of Antibiotics", 2000, vol. 53, p. 1310-1312
[Non-Patent Document 10] "Chinese Chemistry Letters", 2001, vol. 12, p. 903-906
[Non-Patent Document 11] "Journal of Antibiotics", 2000, vol. 53, p. 657-663
[Non-Patent Document 12] "Journal of Medicinal Chemistry", 1995, vol. 38, p. 3806-3812
[Non-Patent Document 13] "Tetrahedron Letters", 1991, vol. 42, p. 6015-6018
[Non-Patent Document 14] "Journal of Organic Chemistry", 2003, vol. 68, p. 8162-8169

DISCLOSURE OF INVENTION

Problems to be Solved by the Invention

An object of the present invention is to provide Hsp90 family protein inhibitors useful in preventing and/or treating for cancer or the like. Another object of the present invention is to provide novel benzenoid ansamycin derivatives useful as therapeutic agents for a disease associated with an Hsp90 family protein or a protein to which an Hsp90 family protein is bound (for example, an antitumor agent, an angiogenic inhibitor, an antibacterial agent, or the like) or the like.

Means for Solving the Problems

The present invention relates to the following (1) to (28):
(1) A benzenoid ansamycin derivative represented by Formula (I)

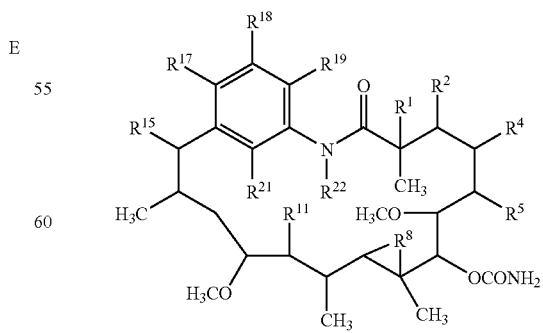

(I)

[wherein $R^1$ and $R^2$ each represent a hydrogen atom or are combined together to form a bond, $R^8$ represents a bond or an oxygen atom, $R^{11}$ represents hydroxy, substituted or unsubstituted lower alkoxy or substituted or unsubstituted lower alkanoyloxy, $R^{15}$ represents a hydrogen atom or methoxy, $R^{22}$ represents a hydrogen atom, substituted or unsubstituted lower alkyl, substituted or unsubstituted lower alkanoyl or substituted or unsubstituted aroyl, $R^4$ and $R^5$ each represent a hydrogen atom or are combined together to form a bond, and (i) when $R^4$ and $R^5$ represent hydrogen atoms;

$R^{18}$ represents a hydrogen atom, hydroxy, cyano, substituted or unsubstituted lower alkyl, substituted or unsubstituted cycloalkyl, substituted or unsubstituted aryl, substituted or unsubstituted aralkyl, substituted or unsubstituted lower alkoxy, substituted or unsubstituted cycloalkyloxy, substituted or unsubstituted aralkyloxy, substituted or unsubstituted heteroalicyclic-oxy, substituted or unsubstituted aryloxy, substituted or unsubstituted heteroaryloxy, substituted or unsubstituted lower alkanoyloxy, substituted or unsubstituted aroyloxy, substituted or unsubstituted lower alkylsulfonyloxy, substituted or unsubstituted arylsulfonyloxy or —$OSiR^{30}R^{31}R^{32}$ (wherein $R^{30}$, $R^{31}$ and $R^{32}$ may be the same or different and each represents lower alkyl or aryl), $R^{21}$ represents hydroxy, substituted or unsubstituted lower alkoxy, substituted or unsubstituted cycloalkyloxy, substituted or unsubstituted aralkyloxy, substituted or unsubstituted heteroalicyclic-oxy, substituted or unsubstituted aryloxy, substituted or unsubstituted heteroaryloxy, substituted or unsubstituted lower alkanoyloxy, substituted or unsubstituted aroyloxy, substituted or unsubstituted lower alkylsulfonyloxy or substituted or unsubstituted arylsulfonyloxy, and $R^{17}$ and $R^{19}$ may be the same or different and each represents a hydrogen atom, hydroxy, halogen, substituted or unsubstituted lower alkylsulfanyl, substituted or unsubstituted lower alkylsulfinyl, substituted or unsubstituted lower alkyl, substituted or unsubstituted cycloalkyl, substituted or unsubstituted aryl or substituted or unsubstituted heteroaryl, and (ii) when $R^4$ and $R^5$ are combined together to form a bond, $R^{18}$ represents a hydrogen atom, hydroxy, cyano, substituted or unsubstituted lower alkyl, substituted or unsubstituted cycloalkyl, substituted or unsubstituted aryl, substituted or unsubstituted aralkyl, substituted or unsubstituted lower alkoxy, substituted or unsubstituted cycloalkyloxy, substituted or unsubstituted aryloxy, substituted or unsubstituted aralkyloxy, substituted or unsubstituted heteroalicyclic-oxy, substituted or unsubstituted heteroaryloxy, substituted or unsubstituted lower alkanoyloxy, substituted or unsubstituted aroyloxy, substituted or unsubstituted lower alkylsulfonyloxy, substituted or unsubstituted arylsulfonyloxy, or —$OSiR^{30}R^{31}R^{32}$ (wherein $R^{30}$, $R^{31}$ and $R^{32}$ have the same meanings as defined above, respectively), $R^{21}$ represents a hydrogen atom, hydroxy, substituted or unsubstituted lower alkoxy, substituted or unsubstituted cycloalkyloxy, substituted or unsubstituted aryloxy, substituted or unsubstituted aralkyloxy, substituted or unsubstituted heteroalicyclic-oxy, substituted or unsubstituted heteroaryloxy, substituted or unsubstituted lower alkanoyloxy, substituted or unsubstituted aroyloxy, substituted or unsubstituted lower alkylsulfonyloxy or substituted or unsubstituted arylsulfonyloxy, and (ii-1) when $R^{18}$ is hydroxy, lower alkoxy or lower alkanoyloxy, and $R^{21}$ is a hydrogen atom, hydroxy or lower alkoxy, $R^{17}$ and $R^{19}$ may be the same or different and each represents a hydrogen atom, halogen, substituted or unsubstituted cycloalkyloxy, substituted or unsubstituted lower alkylsulfanyl, substituted or unsubstituted lower alkylsulfinyl, substituted or unsubstituted lower alkyl, substituted or unsubstituted cycloalkyl, substituted or unsubstituted aryl or substituted or unsubstituted heteroaryl (with the proviso that $R^{17}$ and $R^{19}$ are not simultaneously hydrogen atoms), (ii-2) when $R^{18}$ is hydroxy, lower alkoxy or lower alkanoyloxy, and $R^{21}$ is substituted lower alkoxy, substituted or unsubstituted cycloalkyloxy, substituted or unsubstituted aryloxy, substituted or unsubstituted aralkyloxy, substituted or unsubstituted heteroalicyclic-oxy, substituted or unsubstituted heteroaryloxy, substituted or unsubstituted lower alkanoyloxy, substituted or unsubstituted aroyloxy, substituted or unsubstituted lower alkylsulfonyloxy or substituted or unsubstituted arylsulfonyloxy, $R^{17}$ and $R^{19}$ may be the same or different and each represents a hydrogen atom, hydroxy, halogen, substituted or unsubstituted lower alkoxy, substituted or unsubstituted cycloalkyloxy, substituted or unsubstituted lower alkylsulfanyl, substituted or unsubstituted lower alkylsulfinyl, —$NR^{40}R^{41}$ (wherein $R^{40}$ and $R^{41}$ may be the same or different and each represents a hydrogen atom, substituted or unsubstituted lower alkyl, substituted or unsubstituted cycloalkyl, substituted or unsubstituted lower alkenyl, substituted or unsubstituted lower alkynyl, substituted or unsubstituted aryl, substituted or unsubstituted heteroaryl, or $R^{40}$ and $R^{41}$ are combined together with the adjacent nitrogen atom thereto to form a substituted or unsubstituted nitrogen-containing heterocyclic group), substituted or unsubstituted lower alkyl, substituted or unsubstituted cycloalkyl, substituted or unsubstituted aryl or substituted or unsubstituted heteroaryl, and (ii-3) when $R^{18}$ is a hydrogen atom, cyano, substituted or unsubstituted lower alkyl, substituted or unsubstituted cycloalkyl, substituted or unsubstituted aryl, substituted or unsubstituted aralkyl, substituted lower alkoxy, substituted or unsubstituted cycloalkyloxy, substituted or unsubstituted aryloxy, substituted or unsubstituted aralkyloxy, substituted or unsubstituted heteroalicyclic-oxy, substituted or unsubstituted heteroaryloxy, substituted lower alkanoyloxy, substituted or unsubstituted aroyloxy, substituted or unsubstituted lower alkylsulfonyloxy, substituted or unsubstituted arylsulfonyloxy or —$OSiR^{30}R^{31}R^{32}$ (wherein $R^{30}$, $R^{31}$ and $R^{32}$ have the same meanings as defined above, respectively), $R^{17}$ and $R^{19}$ may be the same or different and each represents a hydrogen atom, hydroxy, halogen, substituted or unsubstituted lower alkoxy, substituted or unsubstituted cycloalkyloxy, substituted or unsubstituted lower alkylsulfanyl, substituted or unsubstituted lower alkylsulfinyl, —$NR^{40}R^{41}$ (wherein $R^{40}$ and $R^{41}$ have the same meanings as defined above, respectively), substituted or unsubstituted lower alkyl, substituted or unsubstituted cycloalkyl, substituted or unsubstituted aryl or substituted or unsubstituted heteroaryl]

or a pharmaceutically acceptable salt thereof.

(2) The benzenoid ansamycin derivative or the pharmaceutically acceptable salt thereof according to (1), wherein $R^1$, $R^2$, $R^4$ and $R^5$ are hydrogen atoms.

(3) The benzenoid ansamycin derivative or the pharmaceutically acceptable salt thereof according to (1), wherein $R^1$ and $R^2$ are combined together to form a bond.

(4) The benzenoid ansamycin derivative or the pharmaceutically acceptable salt thereof according to (1), wherein $R^1$ and $R^2$, and $R^4$ and $R^5$ are combined together to form bonds.

(5) The benzenoid ansamycin derivative or the pharmaceutically acceptable salt thereof according to any of (1) to (4), wherein $R^{18}$ is hydroxy, lower alkoxy or lower alkanoyloxy.

(6) The benzenoid ansamycin derivative or the pharmaceutically acceptable salt thereof according to (5), wherein $R^{21}$ is substituted or unsubstituted lower alkoxy, substituted or unsubstituted cycloalkyloxy, substituted or unsubstituted aryloxy, substituted or unsubstituted aralkyloxy, substituted or unsubstituted heteroalicyclic-oxy, substituted or unsubstituted heteroaryloxy, substituted or unsubstituted lower alkanoyloxy, substituted or unsubstituted aroyloxy, substituted or unsubstituted lower alkylsulfonyloxy or substituted or unsubstituted arylsulfonyloxy.

(7) The benzenoid ansamycin derivative or the pharmaceutically acceptable salt thereof according to (5), wherein $R^{21}$ is substituted or unsubstituted lower alkoxy, substituted or unsubstituted aralkyloxy or substituted or unsubstituted heteroalicyclic-oxy.

(8) The benzenoid ansamycin derivative or the pharmaceutically acceptable salt thereof according to any of (1) to (4), wherein $R^{18}$ is a hydrogen atom, cyano, substituted or unsubstituted lower alkyl, substituted or unsubstituted cycloalkyl, substituted or unsubstituted aryl, substituted or unsubstituted aralkyl, substituted lower alkoxy, substituted or unsubstituted cycloalkyloxy, substituted or unsubstituted aryloxy, substituted or unsubstituted aralkyloxy, substituted or unsubstituted heteroalicyclic-oxy, substituted or unsubstituted heteroaryloxy, substituted lower alkanoyloxy, substituted or unsubstituted aroyloxy, substituted or unsubstituted lower alkylsulfonyloxy, substituted or unsubstituted arylsulfonyloxy or —OSiR$^{30}$R$^{31}$R$^{32}$ (wherein $R^{30}$, $R^{31}$ and $R^{32}$ have the same meanings as defined above, respectively).

(9) The benzenoid ansamycin derivative or the pharmaceutically acceptable salt thereof according to any of (1) to (4), wherein $R^{18}$ is a hydrogen atom, cyano, substituted or unsubstituted lower alkyl, substituted or unsubstituted aroyloxy or —OSiR$^{30}$R$^{31}$R$^{32}$ (wherein $R^{30}$, $R^{31}$ and $R^{32}$ have the same meanings as defined above, respectively).

(10) The benzenoid ansamycin derivative or the pharmaceutically acceptable salt thereof according to any of (1) to (4), wherein $R^{18}$ is a hydrogen atom, cyano or substituted or unsubstituted lower alkyl.

(11) The benzenoid ansamycin derivative or the pharmaceutically acceptable salt thereof according to any of (8) to (10), wherein $R^{21}$ is hydroxy, substituted or unsubstituted lower alkoxy, substituted or unsubstituted aralkyloxy, substituted or unsubstituted heteroalicyclic-oxy, substituted or unsubstituted lower alkanoyloxy or substituted or unsubstituted lower alkylsulfonyloxy.

(12) The benzenoid ansamycin derivative or the pharmaceutically acceptable salt thereof according to any of (8) to (10), wherein $R^{21}$ is hydroxy, substituted or unsubstituted lower alkoxy, substituted or unsubstituted aralkyloxy or substituted or unsubstituted heteroalicyclic-oxy.

(13) The benzenoid ansamycin derivative or the pharmaceutically acceptable salt thereof according to any of (8) to (10), wherein $R^{21}$ is hydroxy.

(14) The benzenoid ansamycin derivative or the pharmaceutically acceptable salt thereof according to any of (6) to (13), wherein $R^{17}$ and $R^{19}$ may be the same or different and each is a hydrogen atom, halogen, substituted or unsubstituted lower alkylsulfanyl or substituted or unsubstituted lower alkylsulfinyl.

(15) The benzenoid ansamycin derivative or the pharmaceutically acceptable salt thereof according to any of (1) to (14), wherein $R^8$ represents a bond.

(16) The benzenoid ansamycin derivative or the pharmaceutically acceptable salt thereof according to any of (1) to (15), wherein $R^{11}$ is hydroxy or lower alkoxy.

(17) The benzenoid ansamycin derivative or the pharmaceutically acceptable salt thereof according to any of (1) to (15), wherein $R^{11}$ is methoxy.

(18) The benzenoid ansamycin derivative or the pharmaceutically acceptable salt thereof according to any of (1) to (17), wherein $R^{15}$ is methoxy.

(19) A pharmaceutical composition which comprises, as an active ingredient, the benzenoid ansamycin derivative or the pharmaceutically acceptable salt thereof described in any of (1) to (18).

(20) An Hsp90 family protein inhibitor which comprises, as an active ingredient, the benzenoid ansamycin derivative or the pharmaceutically acceptable salt thereof described in any of (1) to (18).

(21) A therapeutic and/or preventive agent for a disease associated with an Hsp90 family protein which comprises, as an active ingredient, the benzenoid ansamycin derivative or the pharmaceutically acceptable salt thereof described in any of (1) to (18).

(22) A therapeutic and/or preventive agent for malignant tumor which comprises, as an active ingredient, the benzenoid ansamycin derivative or the pharmaceutically acceptable salt thereof described in any of (1) to (18).

(23) A method for inhibiting an Hsp90 family protein, which comprises administering an effective amount of the benzenoid ansamycin derivative or the pharmaceutically acceptable salt thereof described in any of (1) to (18).

(24) A method for treating and/or preventing a disease associated with an Hsp90 family protein, which comprises administering an effective amount of the benzenoid ansamycin derivative or the pharmaceutically acceptable salt thereof described in any of (1) to (18).

(25) A method for treating and/or preventing malignant tumor, which comprises administering an effective amount of the benzenoid ansamycin derivative or the pharmaceutically acceptable salt thereof described in any of (1) to (18).

(26) Use of the benzenoid ansamycin derivative or the pharmaceutically acceptable salt thereof described in any of (1) to (18) for the manufacture of an Hsp90 family protein inhibitor.

(27) Use of the benzenoid ansamycin derivative or the pharmaceutically acceptable salt thereof described in any of (1) to (18) for the manufacture of a therapeutic and/or preventive agent for a disease associated with an Hsp90 family protein.

(28) Use of the benzenoid ansamycin derivative or the pharmaceutically acceptable salt thereof described in any of (1) to (18) for the manufacture of a therapeutic and/or preventive agent for malignant tumor.

EFFECTS OF THE INVENTION

The present invention provides an Hsp90 family protein inhibitor which comprises, as an active ingredient, a benzenoid ansamycin derivative or a pharmaceutically acceptable salt thereof, and a benzenoid ansamycin derivative or a pharmaceutically acceptable salt thereof having an inhibitory activity on an Hsp90 family protein and useful as an antitumor agent or the like.

BEST MODE FOR CARRYING OUT THE INVENTION

Hereinafter, a compound represented by Formula (I) is referred to as Compound (I). The same is true in other compounds represented by other formulae.

In the definition of groups in Formula (I),

Examples of lower alkyl and lower alkyl moieties in lower alkoxy, lower alkylsulfanyl, lower alkylsulfinyl, lower alkylsulfonyloxy, lower alkanoyl, and lower alkanoyloxy include linear or branched alkyl having 1 to 10 carbon atoms. Specific examples thereof include methyl, ethyl, propyl, isopropyl, butyl, isobutyl, sec-butyl, tert-butyl, pentyl, isopentyl, neopentyl, hexyl, heptyl, octyl, nonyl, and decyl.

Examples of lower alkenyl include linear or branched alkenyl having 2 to 10 carbon atoms. Specific examples thereof include vinyl, allyl, 1-propenyl, butenyl, pentenyl, hexenyl, heptenyl, octenyl, nonenyl, and decenyl.

Examples of lower alkynyl include linear or branched alkynyl having 2 to 10 carbon atoms. Specific examples thereof include ethynyl, propynyl, butynyl, pentynyl, hexynyl, heptynyl, octynyl, nonynyl, and decynyl.

Examples of cycloalkyl and cycloalkyl moieties in cycloalkyloxy include cycloalkyl having 3 to 8 carbon atoms. Specific examples thereof include cyclopropyl, cyclobutyl, cyclopentyl, cyclohexyl, cycloheptyl, and cyclooctyl.

Examples of aralkyl and aralkyl moieties in aralkyloxy include aralkyl having 7 to 16 carbon atoms. Specific examples thereof include benzyl, phenethyl, phenylpropyl, phenylbutyl, phenylpentyl, phenylhexyl, phenylheptyl, phenyloctyl, phenylnonyl, phenyldecyl, naphthylmethyl, naphthylethyl, naphthylpropyl, naphthylbutyl, naphthylpentyl, naphthylhexyl, anthrylmethyl, and anthrylethyl.

Examples of aryl and aryl moieties in aryloxy, arylsulfonyloxy, aroyl, and aroyloxy include aryl having 6 to 14 carbon atoms. Specific examples thereof include phenyl, naphthyl, azulenyl, and anthryl.

Examples of heteroaryl and heteroaryl moieties in heteroaryloxy include five- or six-membered monocyclic heteroaryl containing at least one atom selected from a nitrogen atom, an oxygen atom, and a sulfur atom; and bicyclic or tricyclic condensed-ring heteroaryl obtained by condensation of three- to eight-membered rings and containing at least one atom selected from a nitrogen atom, an oxygen atom, and a sulfur atom. Specific examples thereof include furyl, thienyl, pyroryl, imidazolyl, pyrazolyl, oxazolyl, isoxazolyl, oxadiazolyl, thiazolyl, isothiazolyl, thiadiazolyl, triazolyl, tetrazolyl, pyridyl, pyridazinyl, pyrimidinyl, pyrazinyl, triazinyl, benzofuranyl, benzothiophenyl, benzoxazolyl, benzothiazolyl, isoindolyl, indolyl, indazolyl, benzoimidazolyl, benzotriazolyl, oxazolopyrimidinyl, thiazolopyrimidinyl, pyrrolopyridinyl, pyrrolopyrimidinyl, imidazopyridinyl, purinyl, quinolinyl, isoquinolinyl, cinnolinyl, phthalazinyl, quinazolinyl, quinoxalinyl, and naphthylidinyl.

Examples of heteroalicyclic moieties in heteroalicyclicoxy include a five- or six-membered monocyclic heteroalicyclic group containing at least one atom selected from a nitrogen atom, an oxygen atom, and a sulfur atom; and a bicyclic or tricyclic condensed heteroalicyclic group obtained by condensation of three- to eight-membered rings and containing at least one atom selected from a nitrogen atom, an oxygen atom, and a sulfur atom. Specific examples thereof include aziridinyl, azetidinyl, pyrrolidinyl, piperidino, piperidinyl, azepanyl, 1,2,5,6-tetrahydropyridyl, imidazolidinyl, pyrazolidinyl, piperazinyl, homopiperazinyl, pyrazolinyl, oxiranyl, tetrahydrofuranyl, tetrahydro-2H-pyranyl, 5,6-dihydro-2H-pyranyl, oxazolidinyl, morpholino, morpholinyl, thiozazolidinyl, thiomorpholinyl, 2H-oxazolyl, 2H-thioxazolyl, dihydroindolyl, dihydroisoindolyl, dihydrobenzofuranyl, benzoimidazolidinyl, dihydrobenzooxazolyl, dihydrobenzothioxazolyl, benzodioxolinyl, tetrahydroquinolyl, tetrahydroisoquinolyl, dihydro-2H-chromanyl, dihydro-1H-chromanyl, dihydro-2H-thiochromanyl, dihydro-1H-thiochromanyl, tetrahydroquinoxalinyl, tetrahydroquinazolinyl, and dihydrobenzodioxanyl.

Examples of a nitrogen-containing heterocyclic group formed together with the adjacent nitrogen atom include a five- or six-membered heteromonocyclic group containing at least one nitrogen atom (wherein the heteromonocyclic group may further contain another nitrogen, oxygen, or sulfur atom); and a bicyclic or tricyclic condensed heterocyclic group obtained by condensation of three- to eight-membered rings and containing at least one nitrogen atom (the condensed heterocyclic group may further contain another nitrogen, oxygen, or sulfur atom). Specific examples thereof include aziridinyl, azetidinyl, pyrrolidinyl, piperidino, azepanyl, pyroryl, imidazolidinyl, imidazolyl, pyrazolidinyl, pyrazolinyl, pyrazolyl, piperazinyl, homopiperazinyl, oxazolidinyl, 2H-oxazolyl, thioxazolidinyl, 2H-thioxazolyl, morpholino, thiomorpholinyl, dihydroindolyl, dihydroisoindolyl, indolyl, isoindolyl, tetrahydroquinolyl, tetrahydroisoquinolyl, dihydrobenzooxazolyl, dihydrobenzothioxazolyl, benzoimidazolidinyl, benzoimidazolyl, dihydroindazolyl, indazolyl, benzotriazolyl, pyrrolopyridinyl, pyrrolopyrimidinyl, imidazopyridinyl, and purinyl.

The term "halogen" refers to a fluorine atom, a chlorine atom, a bromine atom, or an iodine atom.

Each of substituted lower alkyl, substituted lower alkoxy, substituted lower alkanoyl, substituted lower alkanoyloxy, substituted lower alkylsulfanyl, substituted lower alkylsulfinyl, substituted cycloalkyl, substituted cycloalkyloxy, substituted lower alkylsulfonyloxy, substituted lower alkenyl, and substituted lower alkynyl has from 1 to the maximal possible number of substituents and preferably has 1 to 3 substituents, wherein the substituents may be the same or different. Examples of the substituent include halogen; hydroxy; cyano; carboxy; sulfanyl; amino; lower alkoxy optionally substituted by Substituent A described below; lower alkylsulfanyl optionally substituted by Substituent A described below; lower alkylamino optionally substituted by Substituent A described below; di(lower alkyl)amino optionally substituted by Substituent A described below; aralkylamino optionally substituted by Substituent A described below; lower alkoxycarbonylamino optionally substituted by Substituent A described below; lower alkanoylamino optionally substituted by Substituent A described below; aroylamino optionally substituted by Substituent A described below; a heteroalicyclic group optionally substituted by Substituent A described below; heteroaryl optionally substituted by Substituent A described below; aryl optionally substituted by Substituent A described below; lower alkoxycarbonyl optionally substituted by Substituent A described below; lower alkanoyloxy optionally substituted by Substituent A described below; and tri(lower alkyl)silyl.

The term "Substituent A" refers to one to three substituents selected from the group consisting of halogen, hydroxy, lower alkoxy, amino, lower alkylamino, di(lower alkyl)amino, nitro, and sulfanyl.

Lower alkyl and lower alkyl moieties in lower alkoxy, lower alkylsulfanyl, lower alkylamino, di(lower alkyl)amino, lower alkoxycarbonylamino, lower alkanoylamino, lower alkoxycarbonyl, lower alkanoyloxy, and tri(lower alkyl)silyl described here have the same meanings as lower alkyl defined above. Aryl and aryl moieties in aroylamino have the same meanings as aryl defined above. An aralkyl moiety in aralkylamino has the same meaning as aralkyl defined above. Heteroaryl, a heteroalicyclic group, and halogen have the same meanings as heteroaryl, the heteroalicyclic moiety in heteroalicyclic-oxy, and halogen, respectively, defined above.

Each of substituted aryl, substituted aryloxy, substituted aroyl, substituted aroyloxy, substituted arylsulfonyloxy, substituted aralkyl, substituted aralkyloxy, substituted heteroaryl, substituted heteroaryloxy, substituted heteroalicyclic-oxy, and a substituted nitrogen-containing heterocyclic group formed together with the adjacent nitrogen atom has from 1 to the maximal possible number of substituents and preferably has 1 to 3 substituents, wherein the substituents may be the same or different. Examples of the substituent include halogen; hydroxy; cyano; carboxy; sulfanyl; amino; lower alkoxy optionally substituted by Substituent A described above; lower alkylsulfanyl optionally substituted by Substituent A described above; lower alkylamino optionally substituted by Substituent A described above; di(lower alkyl)amino optionally substituted by Substituent A described above; aralkylamino optionally substituted by Substituent A described above; lower alkoxycarbonylamino optionally substituted by Substituent A described above; lower alkanoylamino optionally substituted by Substituent A described above; aroylamino optionally substituted by Substituent A described above; a heteroalicyclic group optionally substituted by Substituent A described above; heteroaryl optionally substituted by Substituent A described above; aryl optionally substituted by Substituent A described above; lower alkoxycarbonyl optionally substituted by Substituent A described above; lower alkanoyloxy optionally substituted by Substituent A described above; lower alkyl optionally substituted by Substituent A described above; lower alkanoyl optionally substituted by Substituent A described above; and aroyl optionally substituted by Substituent A described above.

Lower alkyl and lower alkyl moieties in lower alkoxy, lower alkylsulfanyl, lower alkylamino, di(lower alkyl)amino, lower alkoxycarbonylamino, lower alkanoylamino, lower alkoxycarbonyl, lower alkanoyloxy, and lower alkanoyl described here have the same meanings as lower alkyl defined above. Aryl and aryl moieties in aroyl and aroylamino have the same meanings as aryl defined above. An aralkyl moiety in aralkylamino has the same meaning as aralkyl defined above. Heteroaryl, a heteroalicyclic group, and halogen have the same meanings as heteroaryl, the heteroalicyclic moiety in heteroalicyclic-oxy, and halogen, respectively, defined above.

Examples of the pharmaceutically acceptable salt of Compound (I) include pharmaceutically acceptable acid addition salts, metal salts, ammonium salts, organic amine addition salts, and amino acid addition salts. Examples of the pharmaceutically acceptable acid addition salts include inorganic acid salts, such as hydrochloride, hydrobromate, nitrate, sulfate, and phosphate; and organic acid salts, such as acetate, oxalate, maleate, fumarate, citrate, benzoate, and methanesulfonate. Examples of the pharmaceutically acceptable metal salts include alkali metal salts, such as sodium salts and potassium salts; alkaline-earth metal salts, such as magnesium salts and calcium salts; aluminum salts; and zinc salts. Examples of the pharmaceutically acceptable ammonium salts include ammonium salts and tetramethylammonium. Examples of the pharmaceutically acceptable organic amine addition salts include addition salts of morpholine and piperidine. Examples of the pharmaceutically acceptable amino acid addition salts include addition salts of lysine, glycine, phenylalanine, aspartic acid, and glutamic acid.

A method for producing Compound (I) will be described below.

In the following production method, when a group defined is changed under conditions according to the production method or is not appropriate for the implementation of the production method, a target compound can be obtained by a method, which is commonly employed in synthetic organic chemistry, for introducing and removing a protecting group (described in, for example, T. W. Greene; Protective Groups in Organic Synthesis, third edition, John Wiley & Sons Inc, 1999) or the like. Furthermore, according to need, the sequence of reaction steps, for example, a step of introducing a substituent, may be changed.

Production Method 1

Compound (I) may be produced by chemical conversion of a compound, e.g., commercially available a benzenoid ansamycin derivative, such as Herbimycin A, Geldanamycin, 17-AAG, or 17-Dimethylaminogeldanamycin, a known compound, such as Reblastatin, Autolytimycin, or 17-O-Demethylreblastatin, or a benzenoid ansamycin derivative described in WO2005/061461, US2005/0026894, Japanese Unexamined Patent Application Publication No. 1-175970, or "Journal of Medicinal Chemistry", vol. 38, p. 3806-3812 (1995), according to a method described in, for example, US2005/0026894 or WO2005/061461.

Production Method 2

Among Compounds (I), Compound (Ia) in which $R^{21}$ represents hydroxy and $R^{18}$ represents a hydrogen atom or hydroxy may also be produced according to the following steps:

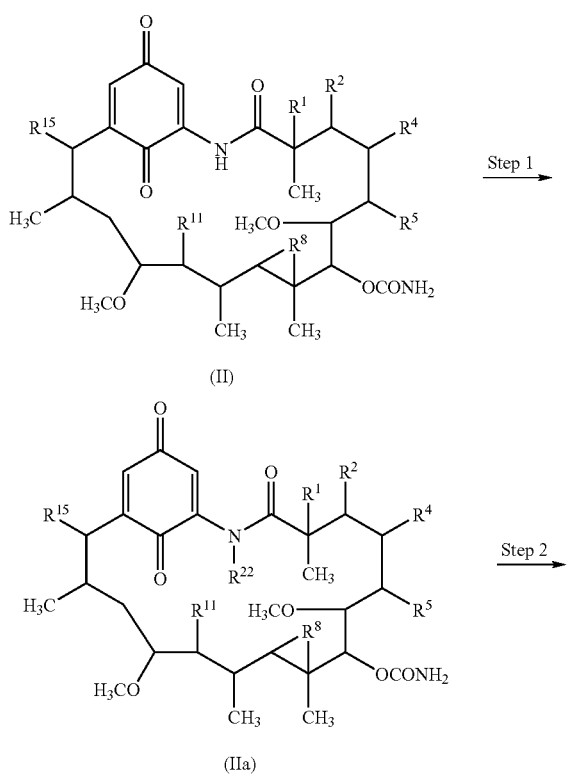

-continued

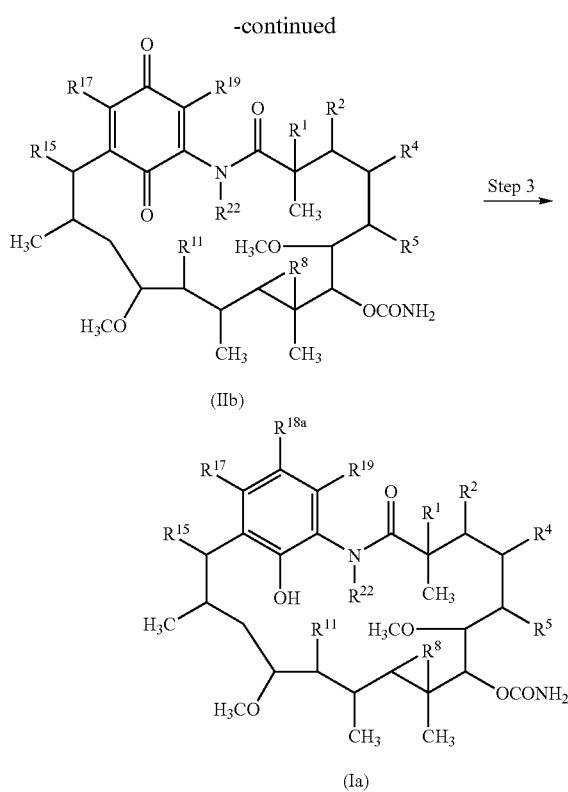

(wherein $R^1$, $R^2$, $R^4$, $R^5$, $R^8$, $R^{11}$, $R^{15}$, $R^{17}$, $R^{19}$, and $R^{22}$ have the same meanings as defined above, respectively; and $R^{18a}$ represents a hydrogen atom or hydroxy)

Step 1 Compound (IIa) may be produced by allowing Compound (II) to react with preferably 1 to 10 equivalents of $R^{22}X$ (wherein $R^{22}$ has the same meaning as defined above; and X represents a leaving group, e.g., a chlorine atom, a bromine atom, an iodine atom, trifluoromethanesulfonyloxy, methanesulfonyloxy, p-toluenesulfonyloxy, or the like) or $R^{22a}{}_2O$ (wherein $R^{22a}$ represents substituted or unsubstituted lower alkanoyl or substituted or unsubstituted aroyl in the definition of $R^{22}$) in an solvent in the presence of preferably 1 to 10 equivalents of a base at a temperature between −78° C. and the boiling point of the solvent used for 5 minutes to 72 hours.

Examples of the solvent include methanol, ethanol, dichloromethane, chloroform, 1,2-dichloroethane, toluene, ethyl acetate, acetonitrile, diethyl ether, tetrahydrofuran (THF), 1,2-dimethoxyethane (DME), dioxane, N,N-dimethylformamide (DMF), N,N-dimethylacetamide (DMA), N-methylpyrrolidone (NMP), pyridine, and water. These may be used alone or as a mixture thereof. Examples of the base include potassium carbonate, potassium hydroxide, sodium hydroxide, potassium tert-butoxide, triethylamine, diisopropylethylamine, pyridine, N,N-dimethylaminopyridine, imidazole, and silver oxide.

In Compound (IIa), a compound in which $R^{22}$ represents methyl may also be produced by allowing Compound (II) to react with diazomethane, trimethylsilyldiazomethane, or the like.

Compound (II) may be obtained as a commercial product. Alternatively, Compound (II) may be obtained by a known method (for example, The Journal of Antibiotics, vol. 37, p. 1264-1267 (1984)).

Step 2 Compound (IIb) may be produced by a known method (for example, The Journal of Antibiotics, vol. 39, p. 415-423 (1986); The Journal of Antibiotics, vol. 37, p. 1264-1267 (1984); US2005/0026894; or The Journal of Medicinal Chemistry, vol. 47, p. 3865-3873 (2004)) using Compound (IIa).

Step 3 Compound (Ia) may be produced by treating Compound (IIb) with an appropriate reductant.

In Compound (Ia), a compound in which $R^{18a}$ represents hydroxy may be produced by allowing Compound (IIb) to react with preferably 1 to 10 equivalents of a reductant, such as sodium borohydride, zinc borohydride, sodium triacetoxyborohydride, samarium iodide, or sodium hydrosulfite, in a solvent at a temperature between −78° C. and the boiling point of the solvent used for 5 minutes to 72 hours.

Examples of the solvent used here include methanol, ethanol, diethyl ether, THF, DME, dioxane, dichloromethane, chloroform, 1,2-dichloroethane, toluene, hexane, and water. These may be used alone or as a mixture thereof.

In Compound (Ia), a compound in which $R^{18a}$ represents a hydrogen atom may be produced by treating Compound (IIb) with preferably 1 to 10 equivalents of a reductant, such as diisobutylaluminum hydride, lithium aluminum hydride, or sodium bis(2-methoxyethoxy)aluminum hydride, in an solvent at a temperature between −78° C. and the boiling point of the solvent used for 5 minutes to 72 hours.

Examples of the solvent used here include diethyl ether, THF, DME, dioxane, dichloromethane, chloroform, 1,2-dichloroethane, toluene, and hexane. These may be used alone or as a mixture thereof.

Production Method 3

Among Compounds (I), Compound (Ib) in which $R^1$, $R^2$, $R^4$ and $R^5$ each represent a hydrogen atom and $R^{18}$ and $R^{21}$ each represent hydroxy may also be produced according to the following steps:

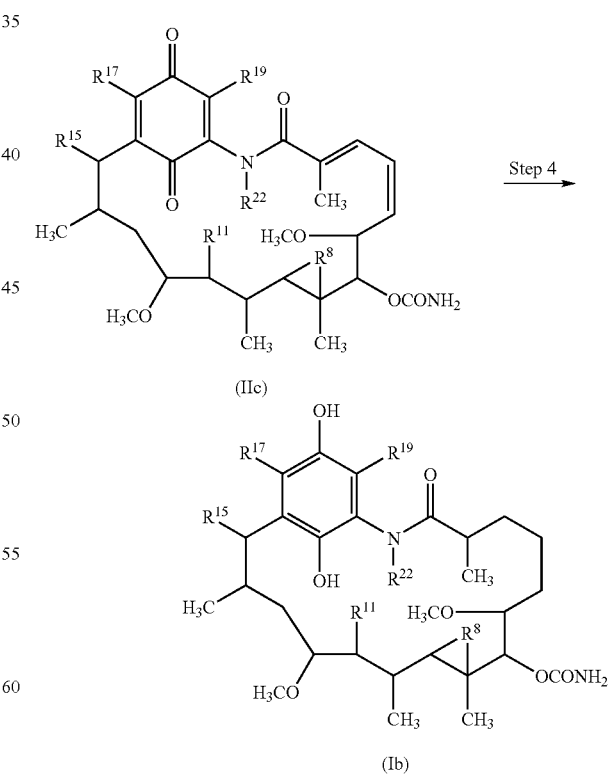

(wherein $R^8$, $R^{11}$, $R^{15}$, $R^{17}$, $R^{19}$ and $R^{22}$ have the same meanings defined above, respectively)

Step 4 Compound (Ib) may be produced by treating Compound (IIc) in a solvent in the presence of an appropriate catalyst at a temperature preferably between −78° C. and the boiling point of the solvent used at atmospheric pressure or under pressure for 5 minutes to 72 hours in a hydrogen atmosphere or in the presence of an appropriate hydrogen source.

Examples of the catalyst include palladium carbon, palladium, palladium hydroxide, palladium acetate, palladium black, and platinum black. Preferably, these catalysts are each used in an amount of 0.01 to 50 percent by weight relative to Compound (IIb). Examples of the hydrogen source include formic acid, ammonium formate, and sodium formate. It is preferred to use 2 equivalents to an excessive amount of the hydrogen source. Examples of the solvent include methanol, ethanol, toluene, ethyl acetate, acetonitrile, diethyl ether, THF, DME, dioxane, DMF, NMP, hexane, and water. These may be used alone or as a mixture thereof.

Compound (IIc) may be obtained as a commercial product. Alternatively, Compound (IIc) may be obtained according to the method described in Production Method 1, Step 2 in Production Method 2, or the like.

Production Method 4

Among Compounds (I), Compound (Id) in which $R^{18}$ represents substituted or unsubstituted lower alkoxy, substituted or unsubstituted cycloalkyloxy, substituted or unsubstituted aralkyloxy, substituted or unsubstituted lower alkanoyloxy, substituted or unsubstituted aroyloxy, substituted or unsubstituted lower alkylsulfonyloxy, substituted or unsubstituted arylsulfonyloxy, substituted or unsubstituted heteroalicyclic-oxy, or —OSiR$^{30}$R$^{31}$R$^{32}$ (wherein R$^{30}$, R$^{31}$, and R$^{32}$ have the same meanings as defined above) may also be produced according to the following step:

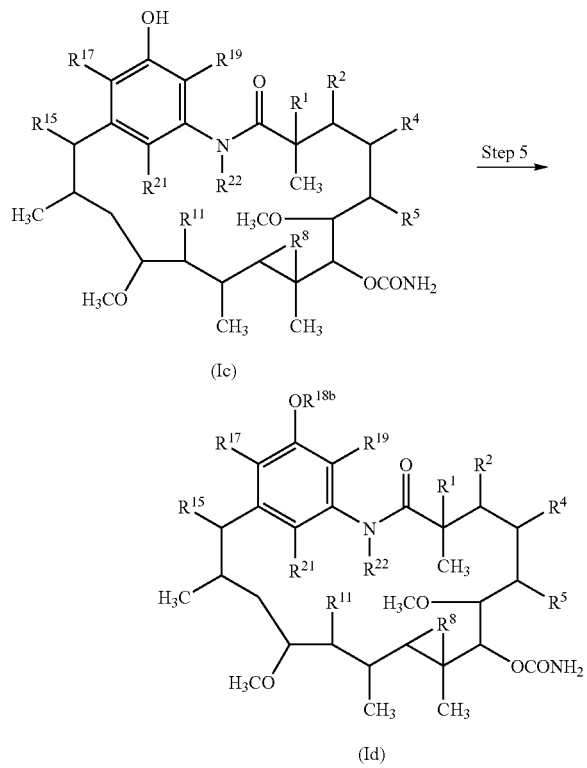

[wherein $R^1$, $R^2$, $R^4$, $R^5$, $R^8$, $R^{11}$, $R^{15}$, $R^{17}$, $R^{19}$, $R^{21}$ and $R^{22}$ have the same meanings as defined above, respectively, and $R^{18b}$ represents substituted or unsubstituted lower alkoxy, substituted or unsubstituted cycloalkyloxy, substituted or unsubstituted aralkyloxy, substituted or unsubstituted lower alkanoyloxy, substituted or unsubstituted aroyloxy, substituted or unsubstituted lower alkylsulfonyloxy, substituted or unsubstituted arylsulfonyloxy, substituted or unsubstituted heteroalicyclic-oxy; a substituted or unsubstituted lower alkyl moiety, a substituted or unsubstituted cycloalkyl moiety, a substituted or unsubstituted aralkyl moiety, a substituted or unsubstituted lower alkanoyl moiety, a substituted or unsubstituted aroyl moiety, a substituted or unsubstituted lower alkylsulfonyl moiety, a substituted or unsubstituted arylsulfonyl moiety, a substituted or unsubstituted heteroalicyclic moiety or SiR$^{30}$R$^{31}$R$^{32}$ (wherein R$^{30}$, R$^{31}$ and R$^{32}$ have the same meanings as defined above, respectively) in OSiR$^{30}$R$^{31}$R$^{32}$ (wherein R$^{30}$, R$^{31}$ and R$^{32}$ have the same meanings as defined above, respectively)].

Step 5 Compound (Id) may be produced by allowing Compound (Ic) to react with preferably 1 to 10 equivalents and more preferably 1 to 2 equivalents of R$^{18b}$X (wherein R$^{18b}$ and X have the same meanings as defined above, respectively) or R$^{18ba}$$_2$O (wherein R$^{18ba}$ represents a substituted or unsubstituted lower alkanoyl moiety, a substituted or unsubstituted aroyl moiety, a substituted or unsubstituted lower alkylsulfonyl moiety, or a substituted or unsubstituted arylsulfonyl moiety in the definition of R$^{18b}$) in a solvent at a temperature between −78° C. and the boiling point of the solvent used in the presence of preferably 1 to 10 equivalents of a base for 5 minutes to 72 hours.

Examples of the base include potassium carbonate, potassium hydroxide, sodium hydroxide, potassium tert-butoxide, triethylamine, diisopropylethylamine, pyridine, N,N-dimethylaminopyridine, imidazole, and silver oxide. Examples of the solvent include methanol, ethanol, acetone, dichloromethane, chloroform, 1,2-dichloroethane, toluene, ethyl acetate, acetonitrile, diethyl ether, THF, DME, dioxane, DMF, DMA, NMP, pyridine, hexane, and water. These may be used alone or as a mixture thereof.

Compound (Ic) may be obtained as a commercial product. Alternatively, Compound (Ic) may be obtained according to the method described in each of Production Methods 1 to 3.

Alternatively, in Compound (Id), Compound (Ida) in which R$^{18b}$ represents substituted or unsubstituted lower alkyl, substituted or unsubstituted cycloalkyl, substituted or unsubstituted aralkyl, or a substituted or unsubstituted heteroalicyclic group may be produced by another method including allowing Compound (Ic) to react with preferably 1 to 10 equivalents of R$^{18bb}$OH (wherein R$^{18bb}$ represents a substituted or unsubstituted lower alkyl moiety, a substituted or unsubstituted cycloalkyl moiety, a substituted or unsubstituted aralkyl moiety, or a substituted or unsubstituted heteroalicyclic group in the definition of R$^{18b}$) in a solvent at a temperature between −78° C. and the boiling point of the solvent used in the presence of preferably 1 to 10 equivalents of a phosphine compound and preferably 1 to 10 equivalents of an azo compound for 5 minutes to 72 hours.

Examples of the phosphine compound include triphenylphosphine and tributylphosphine. Examples of the azo compound include diethyl azodicarboxylate (DEAD), di-tert-butyl azadicarboxylate, diisopropyl azadicarboxylate, N,N,N',N'-tetramethyl azadicarboxamide, 1,1'-(azadicarbonyl) dipiperazine, and N,N,N',N'-tetraisopropyl azadicarboxamide. An example of a preferred combination of the phosphine compound and the azo compound used is a combination of triphenylphosphine and DEAD. Examples of the solvent used here include dichloromethane, chloroform, 1,2-dichloroethane, toluene, ethyl acetate, acetonitrile, diethyl ether, THF, DME, dioxane, DMF, and NMP. These may be used alone or as a mixture thereof.

Production Method 5

Among Compounds (I), Compound (Ifa) and Compound (Ifb) in which $R^{18}$ represents substituted or unsubstituted lower alkanoyloxy or substituted or unsubstituted aroyloxy, $R^{22}$ represents the same moiety as a substituted or unsubstituted lower alkanoyl moiety or a substituted or unsubstituted aroyl moiety in $R^{18}$, and $R^{21}$ represents hydroxy or substituted or unsubstituted lower alkanoyloxy or substituted or unsubstituted aroyloxy equal to $R^{18}$ may also be produced according to the following step:

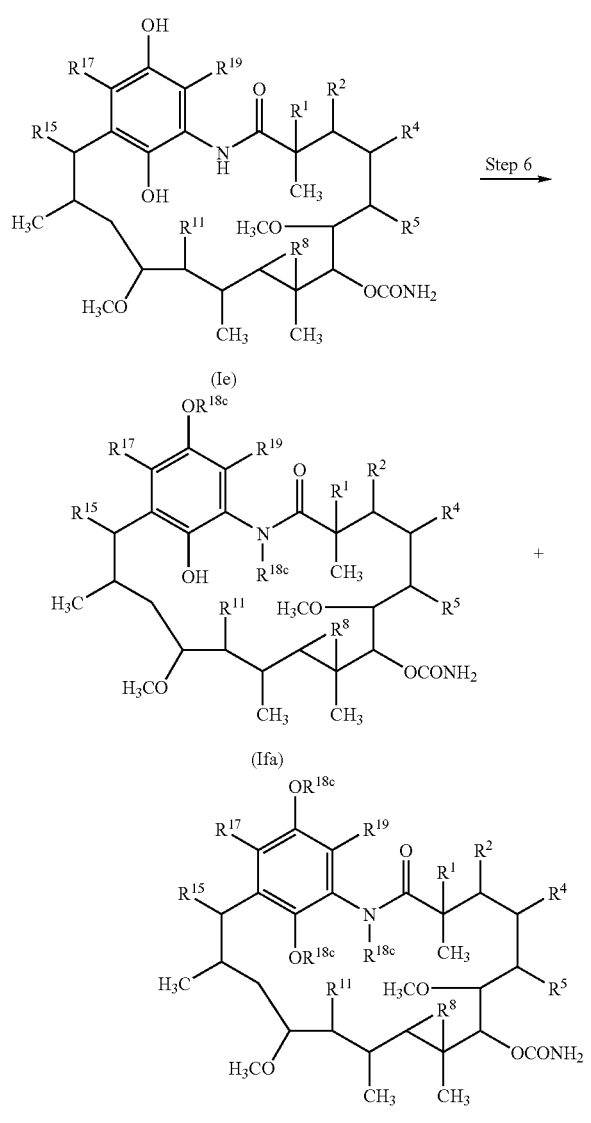

(wherein $R^1$, $R^2$, $R^4$, $R^5$, $R^8$, $R^{11}$, $R^{15}$, $R^{17}$ and $R^{19}$ have the same meanings as defined above, respectively; and $R^{18c}$ represents substituted or unsubstituted lower alkanoyl in substituted or unsubstituted lower alkanoyloxy or substituted or unsubstituted aroyl in substituted or unsubstituted aroyloxy)

Step 6 Compound (Ifa) and Compound (Ifb) may be produced as in Production Method 4 described above from Compound (Ie) with $R^{18c}X$ (wherein $R^{18c}$ and X have the same meanings as defined above, respectively) or $R^{18c}{}_2O$ (wherein $R^{18c}$ has the same meanings as defined above). In this case, preferably, 2 equivalents or more of $R^{18c}X$ (wherein $R^{18c}$ and X have the same meanings as defined above, respectively) or $R^{18c}{}_2O$ (wherein $R^{18c}$ has the same meanings as defined above) is used relative to Compound (Ie).

Compound (Ie) may be obtained as a commercial product. Alternatively, Compound (Ie) may be obtained according to the method described in each of Production Methods 1 to 3.

Production Method 6

Among Compounds (I), Compound (Ig) in which $R^{21}$ represents hydroxy and $R^{18}$ represents substituted or unsubstituted lower alkyl, substituted or unsubstituted cycloalkyl, substituted or unsubstituted aryl, or substituted or unsubstituted aralkyl may also be produced according to the following steps:

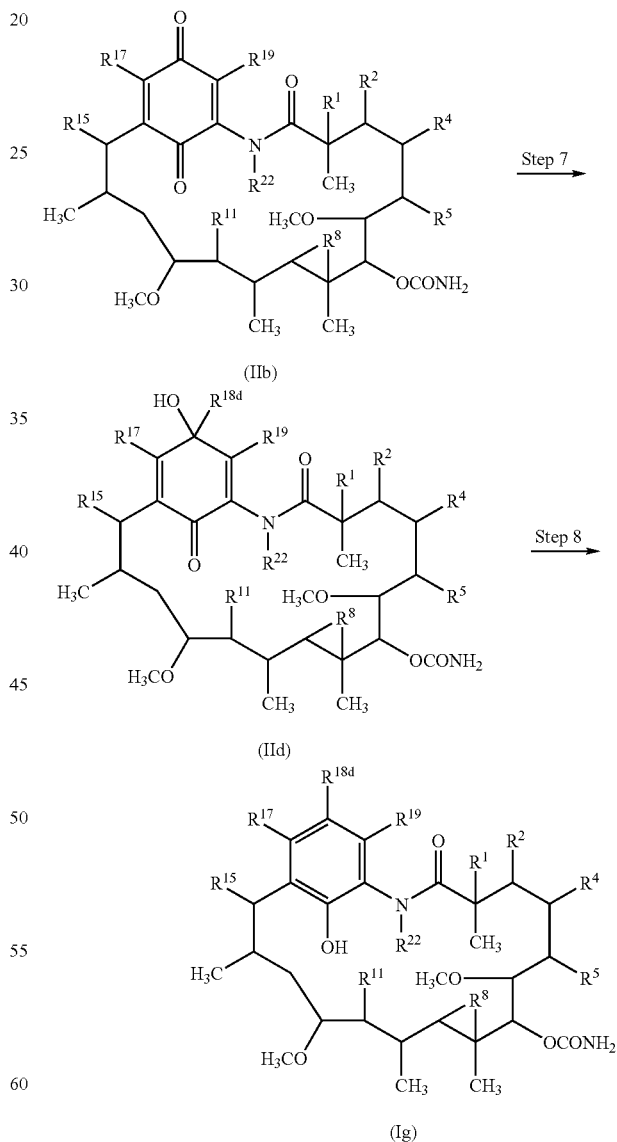

(wherein $R^1$, $R^2$, $R^4$, $R^5$, $R^8$, $R^{11}$, $R^{15}$, $R^{17}$, $R^{19}$, and $R^{22}$ have the same meanings as defined above, respectively; and $R^{18d}$ represents substituted or unsubstituted lower alkyl, substituted or unsubstituted cycloalkyl, substituted or unsubstituted aryl, or substituted or unsubstituted aralkyl)

Step 7 Compound (IId) may be produced by allowing Compound (IIb) to react with preferably 1 to 10 equivalents of $R^{18d}M$ (wherein $R^{18d}$ has the same meanings as defined above; and M represents MgBr, MgCl, or Li) in a solvent at a temperature between −78° C. and the boiling point of the solvent used for 5 minutes to 72 hours.

$R^{18d}M$ (wherein $R^{18d}$ and M have the same meanings as defined above) may be obtained as a commercial product. Alternatively, $R^{18d}M$ may be obtained by or according to a known method [for example, "Dai 5 han Jikken Kagaku Koza 18, Yuki Kagobutsu no Gosei V I, Kinzoku wo Mochiiru Yuki Gosei ($5^{th}$ edition, Experimental Chemistry Course 18, Synthesis of Organic Compound VI, Organic Synthesis with Metal)", $5^{th}$ edition, p. 59, Maruzen (2005)]. Examples of the solvent include toluene, diethyl ether, THF, DME, dioxane, hexane, and dichloromethane. These may be used alone or as a mixture thereof.

Step 8 Compound (Ig) may be produced by treating Compound (IId) with preferably 1 to 10 equivalents of a reductant in a solvent at a temperature between −78° C. and the boiling point of the solvent used for 5 minutes to 72 hours.

Examples of the reductant include sodium borohydride, zinc borohydride, sodium triacetoxyborohydride, diisobutylaluminum hydride, samarium iodide, and sodium hydrosulfite. Examples of the solvent include methanol, ethanol, diethyl ether, THF, DME, dichloromethane, chloroform, 1,2-dichloroethane, toluene, hexane, and water. These may be used alone or as a mixture thereof.

Production Method 7

Among Compounds (I), Compound (Ih) in which $R^{21}$ represents hydroxy and $R^{18}$ represents cyano may also be produced according to the following steps:

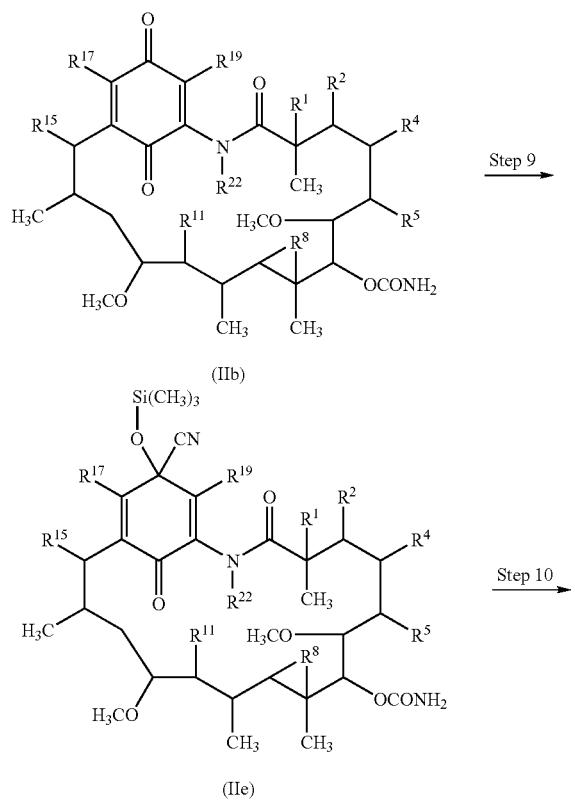

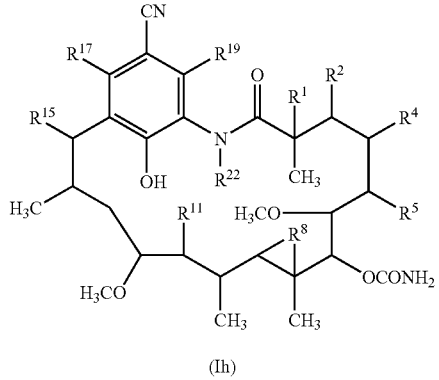

(wherein $R^1$, $R^2$, $R^4$, $R^5$, $R^8$, $R^{11}$, $R^{15}$, $R^{17}$, $R^{19}$, and $R^{22}$ have the same meanings as defined above, respectively)

Step 9 Compound (IIe) may be produced by allowing Compound (IIb) to react with preferably 1 to 10 equivalents of trimethylsilyl cyanide in a solvent at a temperature between −78° C. and the boiling point of the solvent used for 5 minutes to 72 hours, if necessary, in the presence of catalytic amounts of potassium cyanide and 18-crown-6.

Examples of the solvent include dichloromethane, chloroform, 1,2-dichloroethane, diethyl ether, THF, DME, dioxane, toluene, acetonitrile, hexane, heptane, DMF, and NMP. These may be used alone or as a mixture thereof.

Step 10 Compound (Ih) may be produced by treating Compound (IIe) with preferably 1 to 10 equivalents of a reductant in a solvent at a temperature between −78° C. and the boiling point of the solvent used for 5 minutes to 72 hours.

Examples of the reductant include sodium borohydride, zinc borohydride, sodium triacetoxyborohydride, diisobutylaluminum hydride, and samarium iodide. Examples of the solvent include methanol, ethanol, diethyl ether, THF, DME, dioxane, dichloromethane, chloroform, 1,2-dichloroethane, toluene, and water. These may be used alone or as a mixture thereof.

Production Method 8

Among Compounds (I), Compound (Ii) and Compound (Ij) in which $R^{21}$ represents hydroxy and $R^{18}$ represents lower alkyl having —$NR^{50}R^{51}$ {wherein $NR^{50}R^{51}$ represents a group [e.g., amino, lower alkylamino, di(lower alkyl)amino] containing a nitrogen atom attached to lower alkyl in the definition of a substituent in substituted lower alkyl} or —$OR^{52}$ [wherein $OR^{52}$ represents a group (e.g., hydroxy or lower alkoxy) containing an oxygen atom attached to lower alkyl in the definition of a substituent in substituted lower alkyl] at the α position in the definition of $R^{18}$ may also be produced according to the following steps:

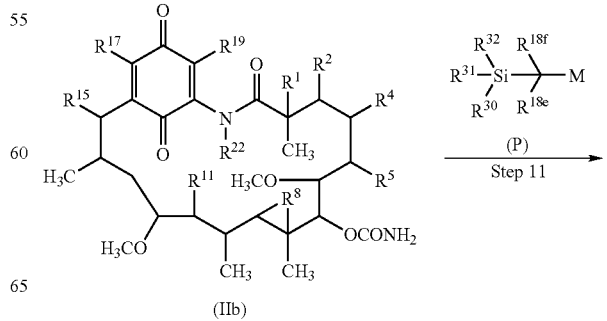

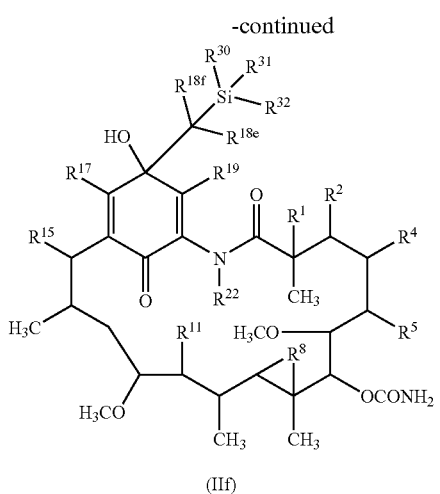

(IIf)

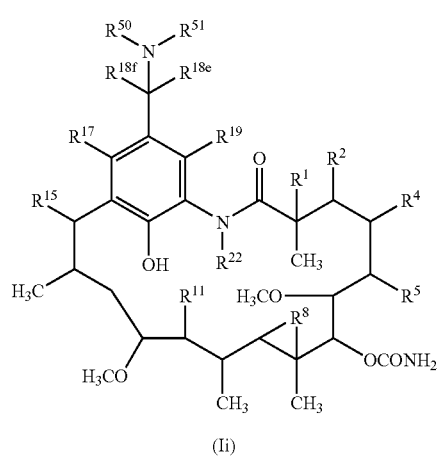

(Ii)

or

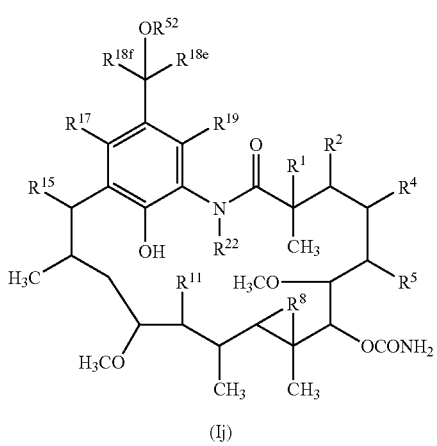

(Ij)

(wherein $R^1$, $R^2$, $R^4$, $R^5$, $R^8$, $R^{11}$, $R^{15}$, $R^{17}$, $R^{19}$, $R^{22}$, $R^{30}$, $R^{31}$, $R^{32}$, and M have the same meanings as defined above, respectively; $R^{18e}$ and $R^{18f}$ are formed together with the adjacent carbon atom to represents a lower alkyl moiety in the above-described lower alkyl group having a substituent at the α position in the definition of $R^{18}$, the lower alkyl moiety being formed together with the adjacent carbon atom; and —$NR^{50}R^{51}$ and —$OR^{52}$ have the same meanings as defined above, respectively)

Step 11 Compound (IIf) may be produced by allowing Compound (IIb) to react with preferably 1 to 20 equivalents of Compound (P) in a solvent at a temperature between −78° C. and boiling point of the solvent used for 5 minutes to 72 hours.

Examples of the solvent include toluene, diethyl ether, THF, DME, dioxane, hexane, and dichloromethane. These may be used alone or as a mixture thereof.

Step 12 Compound (Ii) in which $R^{18}$ represents —$CR^{18e}R^{18f}NR^{50}R^{51}$ (wherein $R^{18e}$, $R^{18f}$, and $NR^{50}R^{51}$ have the same meanings as defined above) may be produced by allowing Compound (IIf) to react with preferably 1 equivalent to an excessive amount of $HNR^{50}R^{51}$ (wherein $NR^{50}R^{51}$ has the same meanings as defined above) in a solvent at a temperature between −78° C. and the boiling point of the solvent used in the presence of preferably 1 to 20 equivalents of a fluorinated agent for 5 minutes to 72 hours.

Examples of the fluorinated agent include tetrabutylammonium fluoride, hydrogen fluoride, hydrogen fluoride-pyridine, cesium fluoride, potassium fluoride, a diethyl ether-boron trifluoride complex, and ammonium fluoride. Tetrabutylammonium fluoride is preferred. Examples of the solvent include toluene, diethyl ether, THF, DME, dioxane, hexane, dichloromethane, methanol, ethanol, 2-propanol, acetonitrile, ethyl acetate, hexane, pyridine, DMF, NMP, and water. These may be used alone or as a mixture thereof.

Compound (Ij) in which $R^{18}$ represents —$CR^{18e}R^{18f}OR^{52}$ (wherein $R^{18e}$, $R^{18f}$, and $OR^{52}$ have the same meanings as defined above) may be produced by allowing Compound (IIf) to react with preferably 1 equivalent to an excessive amount of $HOR^{52}$ (wherein $OR^{52}$ has the same meanings as defined above) in a solvent at a temperature between −78° C. and the boiling point of the solvent used in the presence of preferably 1 to 20 equivalents of a fluorinated agent for 5 minutes to 72 hours.

Examples of the fluorinated agent used include tetrabutylammonium fluoride, hydrogen fluoride, hydrogen fluoride-pyridine, cesium fluoride, potassium fluoride, a diethyl ether-boron trifluoride complex, and ammonium fluoride. Tetrabutylammonium fluoride is preferred. Examples of the solvent include toluene, diethyl ether, THF, DME, dioxane, hexane, dichloromethane, acetonitrile, ethyl acetate, hexane, pyridine, DMF, NMP, and water. These may be used alone or as a mixture thereof.

Among Compounds (Ii) and Compounds (Ij), Compound (Iia) and Compound (Ija) in which $R^{18e}$ and $R^{18f}$ are simultaneously hydrogen atoms may also be produced according to the following step:

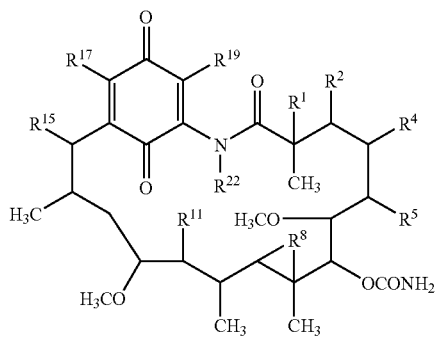

(IIb)

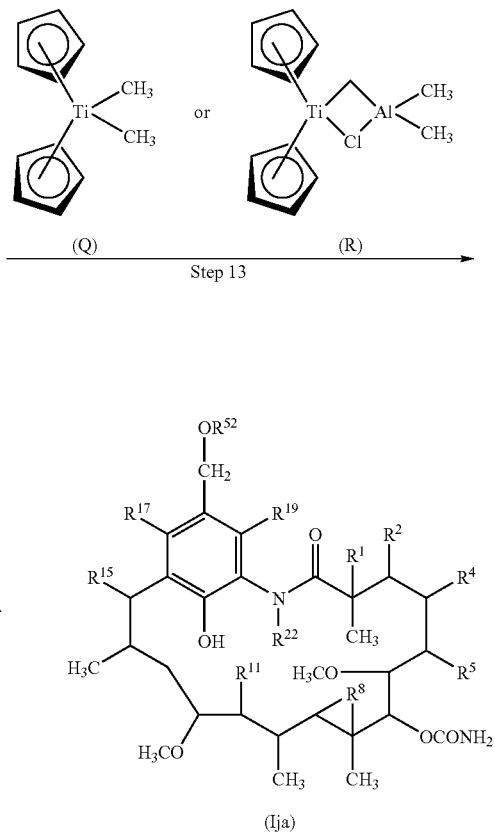

Step 13

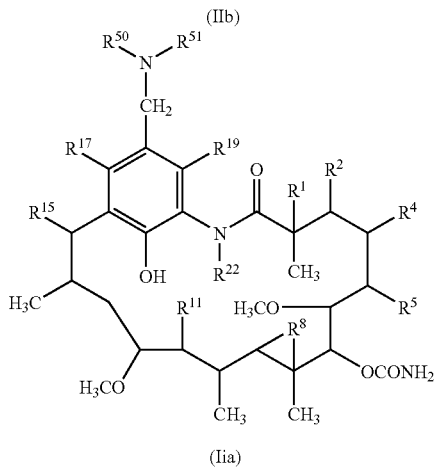

(Iia)  or  (Ija)

(wherein $R^1$, $R^2$, $R^4$, $R^5$, $R^8$, $R^{11}$, $R^{15}$, $R^{17}$, $R^{19}$, $R^{22}$, —$NR^{50}R^{51}$, and —$OR^{52}$ have the same meanings as defined above, respectively)

Compound (Iia) may be produced by allowing Compound (IIb) to react with preferably 1 to 20 equivalents of Tebbe reagent (Compound (R)) or Petasis reagent (Compound (Q)) in a solvent at a temperature between −78° C. and the boiling point of the solvent used for 5 minutes to 72 hours, if necessary, in the presence of preferably a catalytic amount to 10 equivalents of a base, then adding preferably 1 equivalent to an excessive amount of $HNR^{50}R^{51}$ (wherein $HNR^{50}R^{51}$ has the same meanings as defined above), and performing the reaction at a temperature between −78° C. and the boiling point of the solvent used for another 5 minutes to 72 hours.

Examples of the solvent include diethyl ether, diisopropyl ether, THF, DME, benzene, toluene, dichloromethane, chloroform, acetonitrile, DMF, NMP, and pyridine. These may be used alone or as a mixture thereof. In the reaction with $NHR^{50}R^{51}$ (wherein $R^{50}$ and $R^{51}$ have the same meanings as defined above, respectively), water, an alcohol, or the like may be incorporated. Examples of the base include 4-dimethylaminopyridine, imidazole, and triethylamine.

Compound (Ija) may be produced by allowing Compound (IIb) to react with preferably 1 to 20 equivalents of Tebbe reagent (Compound (R)) or Petasis reagent (Compound (Q)) in a solvent at a temperature between −78° C. and the boiling point of the solvent used for 5 minutes to 72 hours, if necessary, in the presence of preferably a catalytic amount to 10 equivalents of a base, then adding preferably 1 equivalent to an excessive amount of $HOR^{52}$ (wherein $OR^{52}$ has the same meanings as defined above), and performing the reaction at a temperature between −78° C. and the boiling point of the solvent used for another 5 minutes to 72 hours.

Examples of the solvent include diethyl ether, diisopropyl ether, THF, DME, benzene, toluene, dichloromethane, chloroform, acetonitrile, DMF, NMP, and pyridine. These may be used alone or as a mixture thereof. Examples of the base include 4-dimethylaminopyridine, imidazole, and triethylamine.

Production Method 9

Among Compounds (I), Compound (Im) in which $R^{18}$ and $R^{21}$ each represent hydroxy and $R^{17}$ represents substituted or unsubstituted lower alkylsulfinyl may also be produced according to the following steps:

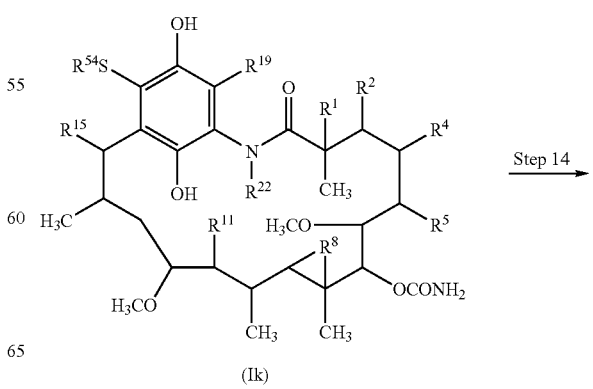

(Ik)

Step 14

-continued

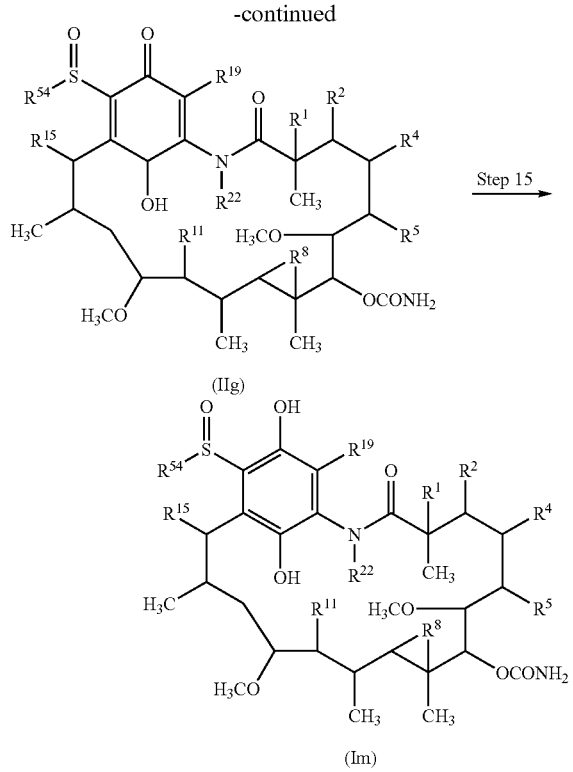

(wherein $R^1$, $R^2$, $R^4$, $R^5$, $R^8$, $R^{11}$, $R^{15}$, $R^{19}$, and $R^{22}$ have the same meanings as defined above, respectively; and $R^{54}$ represents a lower alkyl moiety in substituted or unsubstituted lower alkylsulfanyl and substituted or unsubstituted lower alkylsulfinyl)

Step 14 Compound (IIg) may be produced by treating Compound (Ik) with preferably 1 to 10 equivalents of an oxidant in a solvent at a temperature between −78° C. and the boiling point of the solvent used for 5 minutes to 72 hours.

Examples of the oxidant include cerium(IV) diammonium nitrate, 2,3-dichloro-5,6-dicyano-p-benzoquinone, chloranil, iodosobenzene acetate, iron(III) chloride, silver(I) oxide, silver(I) carbonate, manganese(IV) dioxide, lead(IV) oxide, potassium dichromate(VI), oxygen, vanadium(V) oxide, sodium periodate, m-chloroperbenzoic acid, benzoyl peroxide, and hydrogen peroxide. Examples of the solvent include acetonitrile, water, diethyl ether, THF, DME, dioxane, ethylene glycol, triethylene glycol, glyme, diglyme, methanol, ethanol, 2-propanol, tert-butanol, dichloromethane, chloroform, toluene, ethyl acetate, hexane, DMF, and NMP. These may be used alone or as a mixture thereof.

Step 15 Compound (Im) may be produced by treating Compound (IIg) with preferably 1 to 10 equivalents of a reductant in a solvent at a temperature between −78° C. and the boiling point of the solvent used for 5 minutes to 72 hours.

Examples of the reductant include samarium iodide and sodium hydrosulfite. Examples of the solvent include methanol, ethanol, propanol, diethyl ether, THF, DME, ethyl acetate, dichloromethane, 1,2-dichloroethane, toluene, hexane, and water. These may be used alone or as a mixture thereof.

Compound (Ik) may be obtained as a commercial product. Alternatively, Compound (Ik) may be obtained according to the method described in each of Production Methods 1 to 3, Production Method 12, or the like.

Production Method 10

Among Compounds (I), Compound (Io) in which $R^{18}$ and $R^{21}$ each represent hydroxy and $R^{19}$ represents a bromine atom may also be produced by the following steps:

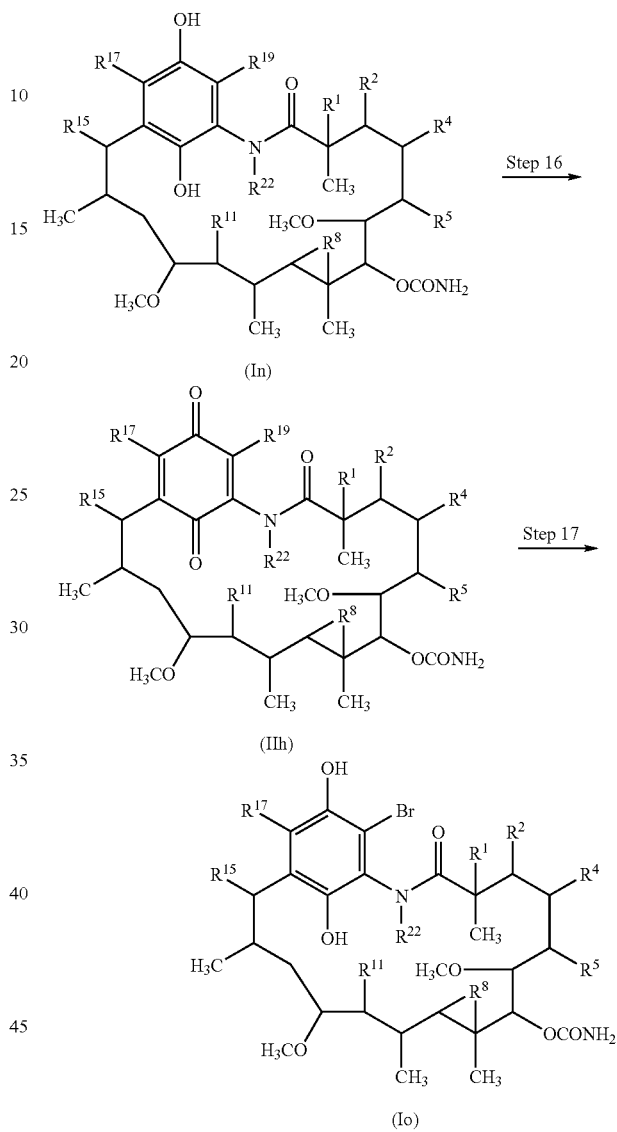

(wherein $R^1$, $R^2$, $R^4$, $R^5$, $R^8$, $R^{11}$, $R^{15}$, $R^{17}$, $R^{18}$, and $R^{22}$ have the same meanings as defined above, respectively)

Step 16 Compound (IIh) may be produced by allowing Compound (In) to react with preferably 2 to 10 equivalents of pyridinium bromide perbromide in a solvent at a temperature between −78° C. and the boiling point of the solvent used for 5 minutes to 72 hours.

Examples of the solvent include methanol, ethanol, acetonitrile, dichloromethane, chloroform, 1,2-dichloroethane, toluene, ethyl acetate, diethyl ether, THF, DME, DMF, and NMP. These may be used alone or as a mixture thereof.

Compound (In) may be obtained as a commercial product. Alternatively, Compound (In) may be obtained according to the method described in each of Production Methods 1 to 3, 9, and 12.

Step 17 Compound (Io) may be produced as in Step 15 in Production Method 9 using Compound (IIh).

Production Method 11

Among Compounds (I), Compound (Iq) in which $R^{21}$ represents substituted or unsubstituted lower alkoxy, substituted or unsubstituted cycloalkyloxy, substituted or unsubstituted aralkyloxy, or substituted or unsubstituted heteroalicyclic-oxy may also be produced according to the following step:

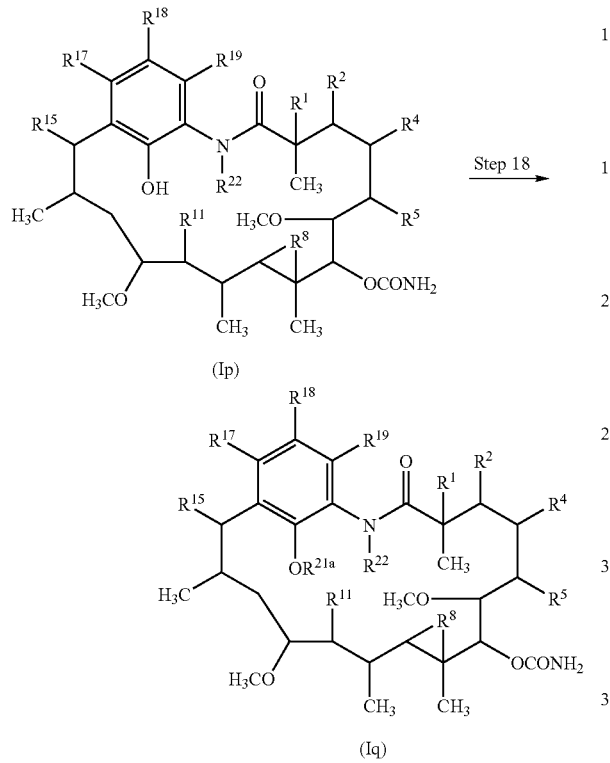

(wherein $R^1$, $R^2$, $R^4$, $R^5$, $R^8$, $R^{11}$, $R^{15}$, $R^{17}$, $R^{18}$, $R^{19}$, and $R^{22}$ have the same meanings as defined above, respectively; and $R^{21a}$ represents a substituted or unsubstituted lower alkyl moiety, a substituted or unsubstituted cycloalkyl moiety, a substituted or unsubstituted aralkyl moiety, or a substituted or unsubstituted heteroalicyclic group in substituted or unsubstituted lower alkoxy, substituted or unsubstituted cycloalkyloxy, substituted or unsubstituted aralkyloxy, or substituted or unsubstituted heteroalicyclic-oxy)

Step 18 Compound (Iq) may be produced by allowing Compound (Ip) to react with preferably 1 to 10 equivalents of $R^{21a}OH$ (wherein $R^{21a}$ has the same meanings as defined above) in a solvent at a temperature between −78° C. and the boiling point of the solvent used for 5 minutes to 7 days in the presence of preferably 1 to 10 equivalents of a phosphine compound and preferably 1 to 10 equivalents of an azo compound.

Examples of the phosphine compound include triphenylphosphine and tributylphosphine. Examples of the azo compound include DEAD, di-tert-butyl azadicarboxylate, diisopropyl azadicarboxylate, N,N,N',N'-tetramethyl azadicarboxamide, 1,1'-(azadicarbonyl)dipiperazine, and N,N,N',N'-tetraisopropyl azadicarboxamide.

An example of a preferred combination of the phosphine compound and the azo compound used is a combination of triphenylphosphine and DEAD.

Examples of the solvent include dichloromethane, chloroform, 1,2-dichloroethane, toluene, ethyl acetate, acetonitrile, diethyl ether, THF, DME, dioxane, DMF, and NMP. These may be used alone or as a mixture thereof.

Compound (Ip) may be obtained as a commercial product. Alternatively, Compound (Ip) may be obtained according to the method described in each of Production Methods 1 to 10 and 12.

Production Method 12

Among Compounds (I), Compound (Ir) in which $R^{18}$ and $R^{21}$ each represent hydroxy and in which one of $R^{17}$ and $R^{19}$ represents substituted or unsubstituted lower alkylsulfanyl, and the other represents a hydrogen atom, or both of $R^{17}$ and $R^{19}$ represent same substituted or unsubstituted lower alkylsulfanyl may also be produced according to the step:

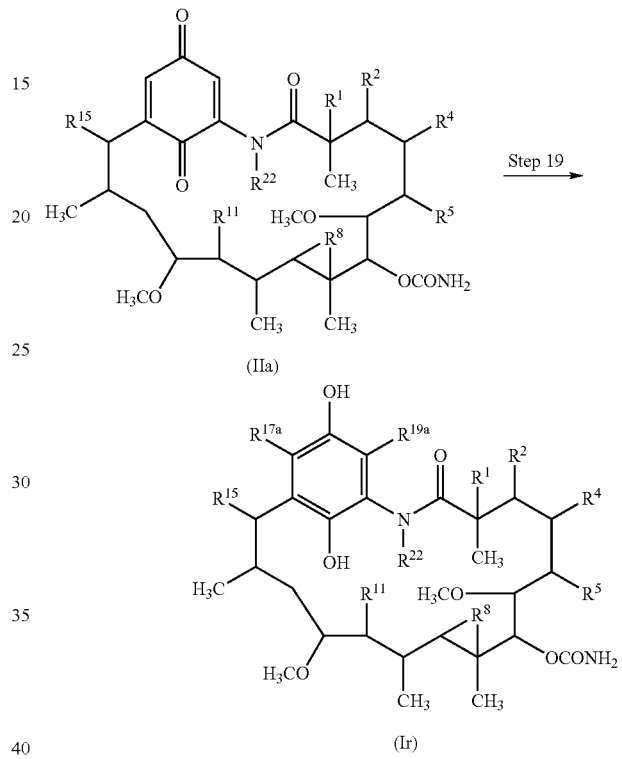

(wherein $R^1$, $R^2$, $R^4$, $R^5$, $R^8$, $R^{11}$, $R^{15}$, and $R^{22}$ have the same meanings as defined above, respectively; and one of $R^{17a}$ and $R^{19a}$ represents substituted or unsubstituted lower alkylsulfanyl, and the other represents a hydrogen atom, or both of $R^{17a}$ and $R^{19a}$ represent same lower alkylsulfanyl)

Step 19 Compound (Ir) may be produced by allowing Compound (IIa) to react with 1 to 20 equivalents of $R^{17aa}SH$ ($R^{17aa}$ represents a lower alkylsulfanyl moiety in substituted or unsubstituted lower alkylsulfanyl) in a solvent at a temperature between −78° C. and the boiling point of the solvent used for 5 minutes to 72 hours.

Examples of the solvent include methanol, ethanol, dichloromethane, chloroform, acetonitrile, toluene, ethyl acetate, diethyl ether, THF, DME, DMF, NMP, pyridine, and water. These may be used alone or as a mixture thereof.

The transformation of functional groups contained in $R^{11}$, $R^{17}$, $R^{18}$, $R^{19}$, $R^{21}$, and $R^{22}$ in Compounds (I) may also be performed by or according to a known method [described in, for example, R. C. Larock. Comprehensive Organic Transformations second edition, Vch Verlagsgesellschaft Mbh (1999)].

Intermediates and target compounds in the above-described production methods may be isolated and purified by isolation purification commonly employed in synthetic organic chemistry, for example, filtration, extraction, washing, drying, concentration, recrystallization, and various types of chromatography. Furthermore, the intermediates may also be used for the subsequent reaction without purification.

Compounds (I) may have a stereoisomer such as a geometric isomer and an optical isomer and a tautomer. The present invention includes all possible isomers including these and mixtures thereof.

In the case where a salt of Compound (I) is targeted, when Compound (I) is obtained in the form of a salt, Compound (I) may be purified as it is. When free Compound (I) is obtained, Compound (I) is dissolved or suspended in an appropriate solvent. An acid or a base is added thereto to form a salt. The resulting salt may be isolated and purified.

Compound (I) and a pharmaceutically acceptable salt thereof may be present in the form of an adduct with water or any of various solvents. The present invention includes these adducts.

Tables 1 and 2 show examples of Compounds (I) obtained in the present invention. However, compounds according to the present invention are not limited thereto.

TABLE 1

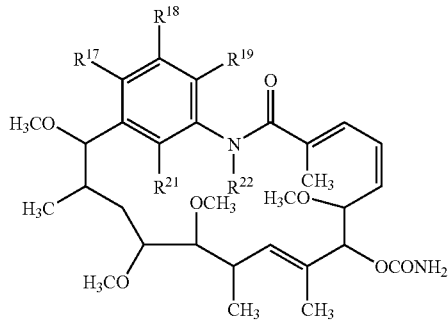

| Example No. | Compound No. | $R^{17}$ | $R^{18}$ | $R^{19}$ | $R^{21}$ | $R^{22}$ |
|---|---|---|---|---|---|---|
| 1 | 2 | H | H | H | OH | H |
| 2 | 4 | H | OCOCH$_3$ | H | OCOCH$_3$ | COCH$_3$ |
| 3 | 5 | H | OCOC$_6$H$_5$ | H | OH | H |
| 4 | 6 | H | OCOC$_6$H$_5$ | H | OH | COC$_6$H$_5$ |
| 5 | 7 | H | OSi(CH$_3$)$_2$—C(CH$_3$)$_3$ | H | OH | H |
| 6 | 8 | H | OSi(CH$_3$)$_2$—C(CH$_3$)$_3$ | H | OSO$_2$CF$_3$ | H |
| 7 | 9 | H | OSi(C$_6$H$_5$)$_2$—C(CH$_3$)$_3$ | H | OH | H |
| 8 | 10 | S(CH$_2$)$_4$CH$_3$ | OH | H | OH | H |
| 9 | 11 | H | OH | S(CH$_2$)$_4$CH$_3$ | OH | H |
| 10 | 12 | SO(CH$_2$)$_4$CH$_3$ | OH | H | OH | H |
| 11 | 13 | S(CH$_2$)$_2$NH—CO$_2$C(CH$_3$)$_3$ | OH | H | OH | H |
| 12 | 14 | Br | OSi(CH$_3$)$_2$—C(CH$_3$)$_3$ | H | OH | H |
| 13 | 15 | Br | OH | H | OH | H |
| 14 | 16 | H | OH | Br | OH | H |
| 15 | 18 | H | CH$_3$ | H | OH | H |
| 16 | 19 | H | CH$_2$CH$_3$ | H | OH | H |
| 17 | 20 | H | CN | H | OH | H |
| 18 | 21 | H | CH$_2$NH$_2$ | H | OH | H |
| 19 | 22 | H | CH$_2$OH | H | OH | H |
| 20 | 23 | H | OSi(CH$_3$)$_2$—C(CH$_3$)$_3$ | H | OCH$_2$C$_6$H$_5$ | H |
| 21 | 24 | H | OH | H | OCH$_2$C$_6$H$_5$ | H |
| 22 | 25 | H | OSi(CH$_3$)$_2$—C(CH$_3$)$_2$ | H | O(CH$_2$)$_2$C$_6$H$_5$ | H |
| 23 | 26 | H | OH | H | O(CH$_2$)$_2$C$_6$H$_5$ | H |
| 24 | 27 | H | OSi(CH$_3$)$_2$—C(CH$_3$)$_3$ | H | OCH$_3$ | H |
| 25 | 28 | H | OH | H | OCH$_3$ | H |
| 26 | 29 | H | OSi(CH$_3$)$_2$C(CH$_3$)$_3$ | H | O(CH$_2$)$_3$N(CH$_3$)$_2$ | H |
| 27 | 30 | H | OH | H | O(CH$_2$)$_3$N(CH$_3$)$_2$ | H |
| 28 | 31 | H | OSi(CH$_3$)$_2$C(CH$_2$)$_3$ | H | O(CH$_2$)$_2$N(CH$_3$)$_2$ | H |
| 29 | 32 | H | OH | H | O(CH$_2$)$_2$N(CH$_3$)$_2$ | H |
| 30 | 33 | H | OSi(CH$_3$)$_2$C(CH$_3$)$_3$ | H | O(CH$_2$)$_2$N(CH$_2$CH$_2$)$_2$ | H |
| 31 | 34 | H | OH | H | O(CH$_2$)$_2$N(CH$_2$CH$_3$)$_2$ | H |
| 32 | 35 | H | OSi(CH$_3$)$_2$C(CH$_3$)$_3$ | H | O—CH$_2$CH$_2$—N(pyrrolidine) | H |

TABLE 1-continued

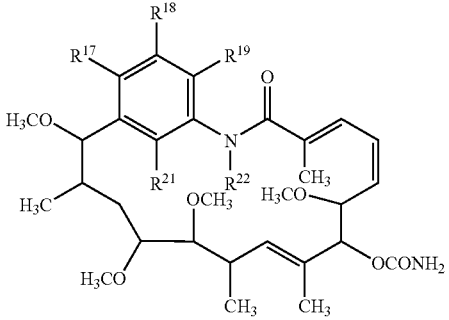

| Example No. | Compound No. | $R^{17}$ | $R^{18}$ | $R^{19}$ | $R^{21}$ | $R^{22}$ |
|---|---|---|---|---|---|---|
| 33 | 36 | H | OH | H | 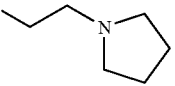 | H |
| 34 | 37 | H | OSi(CH$_2$)$_2$C(CH$_3$)$_3$ | H | 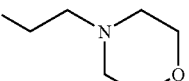 | H |
| 35 | 38 | H | OH | H | 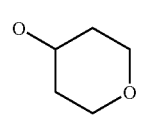 | H |
| 36 | 39 | H | OSi(CH$_3$)$_2$C(CH$_3$)$_3$ | H | 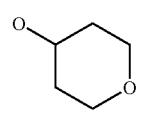 | H |
| 37 | 40 | H | OH | H | 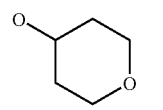 | H |
| 38 | 41 | H | H | H | OCH$_2$CO$_2$CH$_3$ | H |

TABLE 2

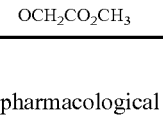

| Example No. | Compound No. | $R^{17}$ | $R^{18}$ | $R^{19}$ | $R^{21}$ | $R^{22}$ |
|---|---|---|---|---|---|---|
| 39 | 42 | H | OH | H | OH | H |

The pharmacological activity of representative Compounds (I) is illustrated below referring to a test example.

Test Example 1

Hsp90 Protein Binding Assay

Human N-terminal recombinant Hsp90 protein (region of amino acids 9 to 236) prepared according to the method described in "Cell", 1997, Vol. 89, p. 239-250 was diluted to 1 µg/mL with Tris-buffered saline (TBS, pH 7.5) and added to each well of a 96-well ELISA assay plate (Greiner) in an amount of 70 µL/well. The plate was incubated overnight at 4° C. to obtain the solid phase.

The supernatant was removed, and Tris-buffered saline containing 1% bovine serum albumin (BSA) was added in an amount of 350 µL/well for blocking.

After the blocking solution was removed, each resulting solid phase was washed by the addition of Tris-buffered saline containing 0.05% Tween 20 (TBST) in an amount of 350 µL/well. This washing procedure was repeated three times.

A test compound having the highest concentration of 0.1 mmol/L was diluted with TBST to prepare eight √10-fold serial dilutions in separate vials. Each of these test compound solutions was added, in an amount of 10 μL/well, to the assay plate containing TBST (90 μL/well) previously added thereto, and the plate was allowed to stand at 24° C. for 1 hour. In this assay, a positive control using dimethyl sulfoxide (final concentration: 0.1 μL/well) and a negative control using Radicicol (final concentration: 0.29 μmol/L) were subjected to the same procedure as the test compound, and these controls were on the same plate which was placed the test compound thereon.

Biotinylated Radicicol ["Bioorganic & Medicinal Chemistry", 2002, vol. 10, p. 3445-3454] represented by Formula (X) was added to give a final concentration of 0.1 μmol/L, and the plate was incubated at 24° C. for further 1 hour for competitive binding reaction to measure the binding activity of the test compound to the immobilized Hsp90 protein. After the reaction mixture was removed, each resulting solid phase was washed by the addition of TBST in an amount of 350 μL/well. This washing procedure was repeated three times.

(manufactured by Nunc Corp.), and using RPMI1640 medium containing 10% fetal calf serum (FCS), preculturing was performed in a 5% carbon dioxide incubator at 37° C. for 5 hours. A DMSO solution of each test compound prepared in a concentration of 10 mmol/L was stepwise diluted with the culture medium and added thereto in a total amount of 100 μL/well. The resulting wells were further cultured in the 5% carbon dioxide incubator at 37° C. for 72 hours. After completion of the culturing, 10 μL of WST-1 (disodium 4-[3-(4-Iodophenyl)-2-(4-nitrophenyl)-2H-5-tetrazolio]-1,3-benzene disulfonate) labeling mixture (manufactured by Roche Diagnostic Corp.) was added to each well, and culturing was performed in the 5% carbon dioxide incubator at 37° C. for 2 hours. Using a microplate spectrophotometer (SpectraMax 340PC384; manufactured by Molecular Devices), the absorbance of each well was measured at 450 nm and 655 nm. Cell growth inhibitory activity was expressed in terms of 50% growth inhibitory concentration (GI50). A method for calculating GI50 is as follows. The value obtained by subtracting

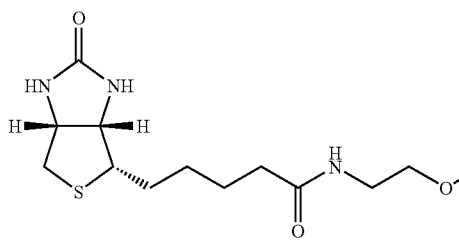
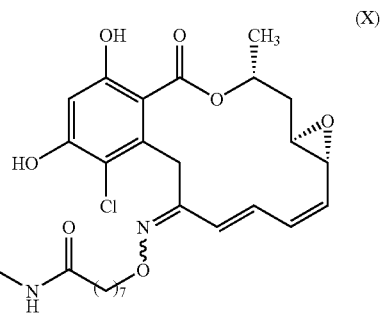

(X)

Europium-labeled streptoavidin (Wallac Oy) was diluted to a final concentration of 0.1 μg/mL with Assay Buffer (Wallac Oy) and added to the wells of the plate in an amount of 100 μL/well. The plate was incubated at room temperature for 1 hour to carry out biotin-avidin binding reaction. After the reaction mixture was removed, each resulting solid phase was washed by the addition of TBST in an amount of 350 μL/well. This washing procedure was repeated five times.

Enhancement solution (Wallac Oy) was added thereto in an amount of 100 μL/well and color developing reaction was carried out at room temperature for 5 minutes, followed by measurement of time-resolved fluorescence (excitation wavelength: 340 nm, measurement wavelength: 615 nm) using Multilabel Counter (ARVO 1420, Wallac Oy).

The binding rate in each well treated the test compound was calculated from the time-resolved fluorescence measured for each well based on the time-resolved fluorescence measured with the positive control taken as 100% binding rate and that with the negative control taken as 0% binding rate.

The results demonstrated that Compounds 1 and 2 inhibited the binding of biotinylated Radicicol to the Hsp90 protein by 50% or more at concentrations 10 μmol/L or less and thus have Hsp90 protein-binding activity. Furthermore, the results demonstrated that Compounds 12, 13, 15, 16, 18, 19, 20, 21, 22, 24, 26, and 42 also inhibited the binding of biotinylated Radicicol to the Hsp90 protein by 50% or more and thus have Hsp90 protein-binding activity.

Test Example 2

Growth Inhibition Test on Human Chronic Myelocytic Leukemia K562 Cells

First, 1,500 cells of human chronic myelocytic leukemia K562 were inoculated into each well of a 96-well microplate the absorbance at 655 nm from the absorbance at 450 nm (absorbance difference) was calculated for each well. The absorbance difference obtained from cells untreated with any of the test compounds was designated as 100%. The absorbance difference obtained from cells treated with the compounds at the test concentrations was compared. The concentration of the compound inhibiting the growth of cells by 50% was calculated and was expressed as GI50.

According to the method, the GI50 of Compound 2 in the present invention is 10 μmol/L or less. Compound 2 exhibits cell growth inhibitory activity against human chronic myelocytic leukemia K562 cells and is thus useful as an antitumor drug. Also in each of Compounds 12, 13, 15, 16, 18, 19, 20, 21, 22, 24, 26, and 42, the GI50 is 10 μmol/L or less. These compounds exhibited cell growth inhibitory activity against human chronic myelocytic leukemia K562 cells.

The results demonstrated that Compound (I) or a pharmaceutically acceptable salt thereof has Hsp90 protein inhibitory activity and is possibly useful as a therapeutic and/or preventive agent for a disease associated with an Hsp90 family protein, for example, solid tumor or malignant tumor such as hematological malignancy, e.g., leukemia.

Compound (I) or a pharmaceutically acceptable salt thereof may be administered alone but, usually, is preferably provided in the form of various pharmaceutical preparations. These pharmaceutical preparations are to be used in animals or humans.

Each of the pharmaceutical preparation associated with the present invention may contain, as an active ingredient, Compound (I) or a pharmaceutically acceptable salt thereof alone or as a mixture with any of active ingredients for another treatment. These medicinal preparations are produced by mixing the active ingredient with one or more pharmaceutically acceptable carriers, such as a diluent, a solvent, and an excipient, and shaping the mixture by any of methods well-known in the technical field of pharmaceutics.

The most effective route of administration is preferably selected for treatment. Examples thereof include oral administration and parenteral administration such as intravenous administration.

Examples of the preparations for administration include tablets and injections.

For example, tablets that are suitable for oral administration may be produced with an excipient such as lactose, a disintegrator such as starch, a lubricant such as magnesium stearate, a binder such as hydroxypropylcellulose, and the like.

For example, injections that are suitable for parenteral administration may be produced with a diluent, such as a saline solution, a glucose solution, or a mixture of a saline solution and a glucose solution, or a solvent.

The dose and the number of doses of Compound (I) or a pharmaceutically acceptable salt thereof will vary depending on the administration route, the age and body weight of a patient, and the nature and degree of severity of the symptom to be treated. In general, in the case of oral administration, the active ingredient is administered in a dose of 0.01 to 1,000 mg and preferably 0.05 to 100 mg per adult once to several times per day. In the case of parenteral administration such as intravenous administration, the active ingredient is administered in a dose of 0.001 to 1,000 mg and preferably 0.01 to 100 mg per adult once to several times per day. However, the dose and the number of doses may vary depending on various conditions described above.

The present invention will be described in further detail by means of examples and reference examples. The scope of the present invention is not limited to these examples.

Example 1

Compound 2

A diisobutylaluminum hydride-hexane solution (0.94 mol/L, 1.74 mmol) was added dropwise to a THF (1.74 mL) solution of Herbimycin A (200 mg, 0.348 mmol) at −78° C. After the mixture was stirred at −78° C. for 45 minutes, a 10% hydrochloric acid-methanol solution (1.5 mL, 3.48 mmol) was added dropwise to the mixture. The temperature of the mixture was gradually increased to room temperature. A saturated aqueous Rochelle salt solution was added thereto. The mixture was stirred for 20 minutes. Insoluble matter was filtered off. An organic layer obtained by extraction of the filtrate with ethyl acetate was dried over anhydrous sodium sulfate. Low-boiling-point components were distilled off under reduced pressure. The resulting residues were purified by thin-layer chromatography (ethyl acetate/hexane=1/1, 3 times) to yield Compound 2 (42 mg, 22%) as a white solid.

ESI Mass (m/z): 561 (M+1)$^+$.

$^1$H-NMR: δ ppm (300 MHz, CDCl$_3$) 0.89 (3H, d, J=6.9 Hz), 1.03-1.07 (2H, m), 1.56-1.85 (4H, m), 1.76 (3H, s), 2.02 (3H, s), 2.36 (1H, brs), 2.65-3.17 (6H, m), 3.27 (3H, s), 3.29-3.36 (4H, m), 3.38 (1H, s), 3.99 (1H, brs), 4.32 (1H, d, J=7.8 Hz), 4.82 (2H, brs), 5.04 (1H, brs), 5.42-5.60 (1H, brs), 5.65-5.85 (1H, m), 6.54 (1H, t, J=11.4 Hz), 6.73 (1H, d, J=7.8 Hz), 6.89 (1H, t, J=7.8 Hz), 7.04 (1H, brs), 8.05-8.34 (2H, brs).

Example 2

Compound 4

Dimethylaminopyridine (130 mg, 1.06 mmol) and triethylamine (0.3 mL, 2.15 mmol) were added to a dichloromethane (5.5 mL) solution of Compound 1 obtained in Reference Example 1 (200 mg, 0.348 mmol). Acetic anhydride (0.165 mL, 1.74 mmol) was added thereto at 0° C. The resulting mixture was stirred at room temperature for 16 hours. Water was added to the mixture. Extraction was performed with chloroform. The resulting organic layer was washed with a saturated saline solution and water and dried over anhydrous sodium sulfate. Low-boiling-point components were distilled off under reduced pressure. The resulting residues were purified by thin-layer chromatography (methanol/chloroform=1/9) to yield Compound 3 (66 mg, 29%) and Compound 4 (110 mg, 46%).

ESI Mass (m/z): Compound 4 720 (M+NH$_4^+$)$^+$.

Example 3

Compound 5

Dimethylaminopyridine (50 mg, 0.412 mmol) and triethylamine (0.115 mL, 0.824 mmol) were added to a dichloromethane (2.0 mL) solution of Compound 1 (119 mg, 0.206 mmol) obtained in Reference Example 1. Acetic anhydride (50 mg, 0.216 mmol) was added thereto at 0° C. The resulting mixture was stirred at room temperature for 14 hours. Water was added to the mixture. Extraction was performed with chloroform. The resulting organic layer was washed with a saturated saline solution and water and dried over anhydrous sodium sulfate. The solvent was distilled off under reduced pressure. The resulting residues were purified by thin-layer chromatography (methanol/chloroform=1/15) to yield Compound 5 (23 mg, 16%) and Compound 6 (26 mg, 16%).

ESI Mass (m/z): Compound 5 698 (M+NH$_4^+$)$^+$.

Example 4

Compound 6

Compound 6 was simultaneously obtained in Example 3 described above.

ESI Mass (m/z): Compound 6 802 (M+NH$_4^+$)$^+$.

Example 5

Compound 7

Imidazole (50 mg, 0.73 mmol) was added to a DMF (1.4 mL) solution of Compound 1 (84 mg, 0.146 mmol) obtained in Reference Example 1. tert-Butyldimethylsilyl chloride (71 mg, 0.471 mmol) was added thereto at 0° C. The resulting mixture was stirred at room temperature for 1 hour. Water was added to the mixture. Extraction was performed with ethyl acetate. The resulting organic layer was washed with a saturated saline solution and dried over anhydrous sodium sulfate. The solvent was distilled off under reduced pressure. The resulting residues were purified by silica-gel column chromatography (methanol/chloroform=0/100→2/98) to yield Compound 7 (40 mg, 40%).

ESI Mass (m/z): 708 (M+NH$_4^+$)$^+$.

$^1$H-NMR: δ ppm (300 MHz, CDCl$_3$) 0.20 (3H, s), 0.21 (3H, s), 0.90 (3H, d, J=6.5 Hz), 0.98 (9H, s), 1.00-1.52 (5H, m), 1.61-1.83 (1H, m), 1.77 (3H, s), 2.03 (3H, s), 2.12-2.43

(1H, m), 2.65-3.38 (12H, m), 3.71-3.96 (1H, m), 4.32 (1H, d, J=8.6 Hz), 4.48-5.17 (1H, m), 5.38-5.60 (1H, m), 5.77 (1H, t, J=10.0 Hz), 6.25 (1H, s), 6.54 (1H, t, J=11.9 Hz), 6.72-7.16 (1H, m), 7.30-7.69 (1H, m), 7.70-7.92 (1H, m), 8.19 (1H, brs).

Example 6

Compound 8

Triethylamine (0.52 mL, 3.76 mmol) was added to a dichloromethane (6.3 mL) solution of Compound 7 (216 mg, 0.313 mmol) obtained in Example 5. Trifluoromethanesulfonyl chloride (0.20 mL, 1.88 mmol) was added thereto at 0° C. The resulting mixture was stirred at room temperature for 2 hours. Water was added to the mixture. Extraction was performed with ethyl acetate. The resulting organic layer was washed with a saturated saline solution and dried over anhydrous sodium sulfate. The solvent was distilled off under reduced pressure. The resulting residues were purified by silica-gel column chromatography (ethyl acetate/hexane=1/3→3/1) to yield Compound 8 (109 mg, 41%).

ESI Mass (m/z): 840 $(M+NH_4^+)^+$.

Example 7

Compound 9

Imidazole (150 mg, 2.20 mmol) was added to a DMF (3.5 mL) solution of Compound 1 (200 mg, 0.348 mmol) obtained in Reference Example 1. tert-Butyldiphenylsilyl chloride (0.44 mL, 1.67 mmol) was added there to at 0° C. The resulting mixture was stirred at room temperature for 17 hour. Water was added to the mixture. Extraction was performed with ethyl acetate. The resulting organic layer was washed with a saturated saline solution and dried over anhydrous sodium sulfate. The solvent was distilled off under reduced pressure. The resulting residues were purified by silica-gel column chromatography (ethyl acetate/hexane=1/3→3/1) to yield Compound 9 (162 mg, 57%).

ESI Mass (m/z): 815 $(M+1)^+$.

Example 8

Compound 10 n-Pentanethiol (0.09 mL, 0.725 mmol) was added to an acetonitrile-water (7:1, 4 mL) solution of Herbimycin A (200 mg, 0.348 mmol). The mixture was stirred at room temperature for 5 hours. A saturated aqueous sodium hydrogencarbonate solution was added to the mixture. Extraction was performed with ethyl acetate. The resulting organic layer was washed with a saturated saline solution and dried over anhydrous sodium sulfate. The solvent was distilled off under reduced pressure. The resulting residues were purified by thin-layer chromatography (ethyl acetate/hexane=3/1) to yield Compound 10 (52 mg, 22%) and Compound 11 (38 mg, 16%).

ESI Mass (m/z): 679 $(M+H)^+$.

$^1$H-NMR: δ ppm (300 MHz, CDCl$_3$) 0.89 (3H, t; J=7.2 Hz), 0.90-1.00 (4H, m), 1.01 (3H, d, J=6.3 Hz), 1.23-1.42 (6H, m), 1.54 (5H, m), 1.75 (3H, s), 2.40-2.57 (1H, m), 2.62-2.80 (2H, m), 3.02-3.31 (3H, m), 3.21 (3H, s), 3.25 (3H, s), 3.40 (3H, s), 3.48 (3H, s), 3.98-4.56 (2H, m), 4.76 (2H, brs), 5.03 (1H, d, J=7.5 Hz), 5.16-5.51 (2H, m), 6.36 (1H, t, J=11.4 Hz), 6.49 (1H, s), 6.51-7.11 (2H, m), 7.11-7.79 (1H, m).

Example 9

Compound 11

Compound 11 was simultaneously obtained in Example 8 described above.

ESI Mass (m/z): 679 $(M+H)^+$.

$^1$H-NMR: δ ppm (300 MHz, CDCl$_3$) 0.84 (3H, d, J=6.6 Hz), 0.89 (1H, t, J=6.6 Hz), 1.11-1.45 (9H, m), 1.45-1.70 (4H, m), 1.78 (3H, s), 2.05 (3H, s), 2.20-2.43 (1H, m), 2.62 (2H, t, J=7.5 Hz), 2.71-3.00 (7H, m), 3.22 (3H, s), 3.26-3.38 (7H, m), 4.31 (1H, d, J=9.0 Hz), 4.68-5.07 (2H, m), 4.99 (1H, s), 5.50 (1H, d, J=9.6 Hz), 5.83 (1H, t, J=10.5 Hz), 5.56 (1H, t, J=11.4 Hz), 6.75 (1H, s), 6.86-7.07 (1H, m), 8.04 (1H, s), 8.30 (1H, s).

Example 10

Compound 12

Cerium(IV) diammonium nitrate (73 mg, 0.13 mmol) was added to an acetonitrile-H$_2$O (10:1, 3.0 mL) solution of Compound 10 (30 mg, 0.044 mmol) obtained in Example 8 at 0° C. The mixture was stirred for 10 minutes. Water was added to the mixture. Extraction was performed with chloroform. The resulting organic layer was dried over anhydrous sodium sulfate. The solvent was distilled off under reduced pressure. The resulting residues were purified by thin-layer chromatography (ethyl acetate/hexane=1/1) to yield Compound 50 (22 mg, 72%).

Sodium periodate (7.0 mg, 0.031 mmol) was added to a methanol (0.20 mL) solution of Compound 50 (13 mg, 0.019 mmol) at 0° C. The resulting mixture was stirred at room temperature for 18 hours. Water was added to the mixture. Extraction was performed with ethyl acetate. The resulting organic layer was dried over anhydrous sodium sulfate. The solvent was distilled off under reduced pressure. The resulting residues were purified by thin-layer chromatography (methanol/chloroform=1/9) to yield Compound 51 (6.5 mg, 49%).

An aqueous 10% sodium dithionite solution (0.35 mL, 0.20 mmol) was added dropwise to an ethyl acetate (0.50 mL) solution of Compound 51 (6.0 mg, 0.087 mmol) at room temperature. The resulting mixture was stirred at room temperature for 1.5 hours. The mixture was subjected to extraction with ethyl acetate. The resulting organic layer was washed with a saturated saline solution and dried over anhydrous sodium sulfate. The solvent was distilled off under reduced pressure. The resulting residues were purified by thin-layer chromatography (ethyl acetate/hexane=1/1) to yield Compound 12 (3.3 mg, 55%).

ESI Mass (m/z): 695.2 $(M+H)^+$.

$^1$H-NMR: δ ppm (270 MHz, CDCl$_3$) 0.80-0.97 (7H, m), 1.15-1.60 (12H, m), 1.78 (3H, s), 1.83-1.96 (1H, m), 2.04 (3H, s), 2.26-2.50 (1H, m), 2.73-3.02 (5H, m), 3.02-3.19 (1H, m), 3.19-3.50 (10H, m), 4.29 (1H, d, J=8.9 Hz), 4.71 (2H, brs), 5.01 (1H, s), 5.51 (1H, d, J=9.5 Hz), 5.83 (1H, t, J=9.7 Hz), 6.56 (1H, t, J=11.1 Hz), 6.88-7.16 (1H, m), 7.97 (1H, s), 8.32 (1H, brs), 10.36 (1H, s).

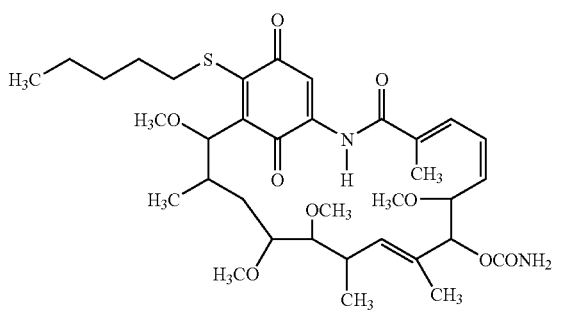

Compound 50

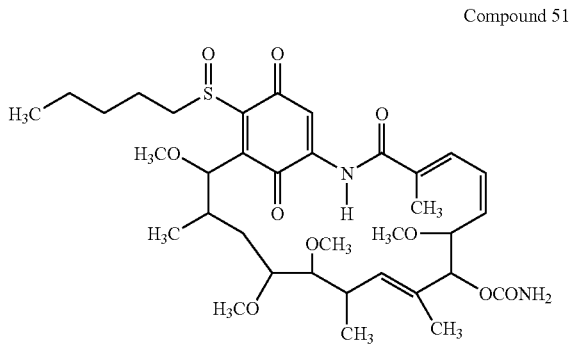

Compound 51

Example 11

Compound 13 tert-Butyl-N-(2-mercaptoethyl)carbamate (0.18 mL, 1.0 mmol) was added to an acetonitrile-water (7:1, 4.0 mL) solution of Herbimycin A (200 mg, 0.35 mmol). The mixture was stirred at room temperature for 4.5 hours. A saturated aqueous sodium hydrogencarbonate solution was added to the mixture. Extraction was performed with ethyl acetate. The resulting organic layer was washed with a saturated saline solution and dried over anhydrous sodium sulfate. The solvent was distilled off under reduced pressure. The resulting residues were purified by silica-gel column chromatography (methanol/chloroform=2/98) to yield Compound 13 (88 mg, 34%).

ESI Mass (m/z): 752.2 (M+H)$^+$.

$^1$H-NMR: δ ppm (270 MHz, CDCl$_3$) 0.84 (3H, d, J=6.6 Hz), 1.11-1.37 (6H, m), 1.49 (9H, s), 1.79 (3H, s), 2.05 (3H, s), 2.20-2.44 (1H, m), 2.68-3.05 (8H, m), 3.23 (3H, s), 3.24-3.35 (2H, m), 3.36 (3H, s), 3.39 (3H, s), 4.30 (1H, d, J=9.0 Hz), 4.78 (2H, brs), 4.87-4.98 (1H, m), 4.99 (1H, s), 5.50 (1H, d, J=9.3 Hz), 5.84 (1H, t, J=10.2 Hz), 6.57 (1H, t, J=11.1 Hz), 6.84 (1H, s), 6.85-7.05 (1H, m), 8.05 (1H, s), 8.09 (1H, brs), 8.29 (1H, s).

Example 12

Compound 14

N-Bromosuccinimide (77 mg, 0.43 mmol) was added to a dichloromethane (2.7 mL) solution of Compound 7 (300 mg, 0.44 mmol) obtained in Example 5 at −78° C. After the temperature of the mixture was increased to room temperature over a period of 1 hour, water was added to the mixture. Extraction was performed with chloroform. The resulting organic layer was dried over anhydrous sodium sulfate. The solvent was distilled off under reduced pressure. The resulting residues were redispersed in ethyl acetate to obtain Compound 14 (170 mg, 51%).

ESI Mass (m/z): 769.0, 771.2 (M+NH$_4^+$)$^+$.

Example 13

Compound 15

Ammonium fluoride (23 mg, 0.59 mmol) was added to methanol (5.9 mL) of Compound 14 (45 mg, 0.059 mmol) obtained in Example 12. The mixture was stirred at room temperature for 1.5 hours. The solvent was distilled off under reduced pressure. The resulting residues were purified by thin-layer chromatography (methanol/chloroform=1/15) to yield Compound 15 (37 mg, 95%). ESI Mass (m/z): 672.2, 674.2 (M+NH$_4^+$)$^+$.

$^1$H-NMR: δ ppm (300 MHz, CDCl$_3$) 0.83 (3H, d, J=6.9 Hz), 1.23-1.33 (1H, m), 1.28 (3H, d, J=5.7 Hz), 1.47-1.62 (4H, m), 1.78 (3H, s), 2.24-2.43 (1H, m), 2.67-3.08 (6H, m), 3.22 (3H, s), 3.37 (6H, s), 4.31 (1H, d, J=9.6 Hz), 4.52 (1H, d, J=10.2 Hz), 4.72 (2H, brs), 4.99 (1H, s), 5.57-5.48 (2H, m), 5.85 (1H, t, J=10.5 Hz), 6.57 (1H, t, J=11.1 Hz), 6.77-7.01 (1H, m), 8.09 (1H, brs), 8.12 (1H, s), 8.22 (1H, s).

Example 14

Compound 16

Pyridinium bromide perbromide (40 mg, 0.13 mmol) was added to a methanol-chloroform solution (1:1, 1.6 mL) of Compound 1 (40 mg, 0.069 mmol) obtained in Reference Example 1 at −78° C. The mixture was stirred for 5 hours. The temperature of the mixture was increased to room temperature over a period of 2 hours. Water was added to the mixture. Extraction was performed with ethyl acetate. The resulting organic layer was washed with a saturated saline solution and dried over anhydrous sodium sulfate. The solvent was distilled off under reduced pressure. The resulting residues were redispersed in ethyl acetate-hexane (1:2) to obtain Compound 52 (18 mg, 65%) [Compound 52 ESI Mass (m/z): 670.1, 672.1 (M+NH$_4^+$)$^+$].

A 10% aqueous sodium dithionite solution (1.1 mL, 0.63 mmol) was added to an ethyl acetate (1.5 mL) solution of Compound 52 (18 mg, 0.028 mmol) obtained. The mixture was stirred at room temperature for 30 minutes and was then subjected to extraction with ethyl acetate. The resulting organic layer was washed with a saturated saline solution and dried over anhydrous sodium sulfate. The solvent was distilled off under reduced pressure. The resulting residues were redispersed in ethyl acetate-hexane (1:9) to obtain Compound 16 (13 mg, 72%).

ESI Mass (m/z): 655.1, 657.1 (M+H)$^+$.

$^1$H-NMR: δ ppm (300 MHz, CDCl$_3$) 0.77-1.19 (9H, m), 1.37-1.88 (6H, m), 2.39-2.60 (1H, m), 2.94-3.12 (1H, m), 3.12-3.38 (8H, m), 3.42 (3H, s), 3.49 (3H, s), 4.01-4.43 (2H, m), 4.62 (2H, brs), 4.95-5.39 (4H, m), 6.33 (1H, t, J=11.7 Hz), 6.48-6.81 (1H, m), 6.92-7.19 (1H, m), 7.30-7.72 (1H, m).

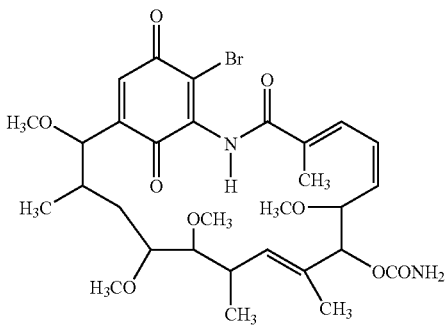

Compound 52

Example 15

Compound 18

A methylmagnesium chloride-THF solution (3.0 mol/L, 1.9 mL, 5.5 mmol) was added to a THF (14 mL) solution of Herbimycin A (400 mg, 0.70 mmol) at −78° C. The temperature of the mixture was increased to −60° C. over a period of 1 hour. Water was added to the mixture. Extraction was performed with ethyl acetate. The resulting organic layer was washed with a saturated saline solution and dried over anhydrous sodium sulfate. The solvent was distilled off under reduced pressure to obtain residues. The resulting residues (500 mg) were used for the subsequent reaction without purification.

A zinc borohydride-ether solution (0.13 mol L, 54 mL, 7.0 mmol) was added to a THF (17 mL) solution of the resulting residues (500 mg) at 0° C. The temperature of the mixture was increased to room temperature. The mixture was stirred for 2 hours and was then subjected to extraction with ethyl acetate. The resulting organic layer was washed with a saturated saline solution and dried over anhydrous sodium sulfate. The solvent was distilled off under reduced pressure. The resulting residues were purified by silica-gel column chromatography (methanol/chloroform=5/95) to yield Compound 18 (87 mg, 22%, 2 steps).

ESI Mass (m/z): 575.2 (M+H)$^+$.

$^1$H-NMR: δ ppm (300 MHz, CDCl$_3$) 0.89 (3H, d, J=6.8 Hz), 1.00-1.21 (3H, m), 1.21-1.58 (2H, m), 1.68-1.97 (4H, m), 2.02 (3H, s), 2.20-2.43 (1H, m), 2.28 (3H, s), 2.71-3.29 (5H, m), 3.27 (3H, s), 3.32 (3H, s), 3.36 (3H, s), 3.92 (1H, brs), 4.31 (1H, d, J=8.1 Hz), 4.89 (2H, brs), 5.03 (1H, s), 5.50 (1H, d, J=6.8 Hz), (1H, t, J=10.0 Hz), 6.46-6.73 (2H, m), 6.79-7.23 (1H, m), 7.67-8.51 (1H, m), 8.03 (1H, brs), 8.14 (1H, brs).

Example 16

Compound 19

An ethylmagnesium bromide-THF solution (3.0 mol/L, 0.087 mL, mmol) was added to a THF (1.7 mL) solution of Herbimycin A mg, 0.17 mmol) at −78° C. The temperature of the mixture was increased to −60° C. over a period of 4 hours. Water was added to the mixture. Extraction was performed with ethyl acetate. The resulting organic layer was washed with a saturated saline solution and dried over anhydrous sodium sulfate. The solvent was distilled off under reduced pressure to obtain residues. The resulting residues were used for the subsequent reaction without purification.

Sodium borohydride (35 mg, 0.93 mmol) was added to a methanol (1.7 mL) solution of the resulting residues at 0° C. The mixture was stirred at room temperature for 2 hours. Water was added to the mixture. Extraction was performed with ethyl acetate. The resulting organic layer was washed with a saturated saline solution and dried over anhydrous sodium sulfate. The solvent was distilled off under reduced pressure. The resulting residues were purified by thin-layer chromatography (ethyl acetate/hexane=2/1) to yield Compound 19 (11 mg, 11%, 2 steps).

ESI Mass (m/z): 589.4 (M+H)$^+$.

$^1$H-NMR: δ ppm (300 MHz, CDCl$_3$) 0.89 (3H, d, J=6.6 Hz), 0.99-1.46 (7H, m), 1.76 (3H, s), 2.02 (3H, s), 2.19-2.45 (1H, m), 2.58 (2H, q, J=7.5 Hz), 2.76-3.17 (5H, m), 3.21-3.46 (1H, m), 3.26 (3H, s), 3.33 (3H, s), 3.37 (3H, s), 3.79-4.07 (1H, m), 4.31 (1H, d, J=7.8 Hz), 4.79 (2H, brs), 5.04 (1H, s), 5.40-5.61 (1H, m), 5.66-5.78 (1H, m), 6.48-6.63 (3H, m), 6.82-7.21 (1H, m), 7.74-8.18 (1H, m), 8.09 (1H, brs), 8.16 (1H, brs).

Example 17

Compound 20

Trimethylsilyl cyanide (28 μL, 0.21 mmol), potassium cyanide (1.0 mg), and 18-crown-6 (1.0 mg) were added to a dichloromethane (0.87 mL) solution of Herbimycin A (100 mg, 0.17 mmol). After the mixture was stirred at room temperature for 20 hours, water was added thereto. Extraction was performed with ethyl acetate. The resulting organic layer was washed with a saturated saline solution and dried over anhydrous sodium sulfate. The solvent was distilled off under reduced pressure to obtain residues. The resulting residues (120 mg) were used for the subsequent reaction without purification.

A samarium iodide-THF solution (1.0 mol/L, 1.6 mL, 1.6 mmoL) was added dropwise to a methanol (0.50 mL) solution of the resulting residues (120 mg) obtained at −78° C. After the mixture was stirred at −20° C. for 2.5 hours, water was added to the mixture. Extraction was performed with ethyl acetate. The resulting organic layer was washed with a saturated saline solution and dried over anhydrous sodium sulfate. The solvent was distilled off under reduced pressure. The resulting residues were purified by thin-layer chromatography (ethyl acetate/hexane=2/1) to yield Compound 20 (9.7 mg, 9%, 2 steps).

ESI Mass (m/z): 525 (M-OCONH$_2$)$^+$.

$^1$H-NMR: δ ppm (300 MHz, CDCl$_3$) 0.93 (3H, d, J=6.9 Hz), 0.95-1.18 (3H, m), 1.25-1.85 (3H, m), 1.76 (3H, s), 2.05 (3H, s), 2.20-2.48 (1H, m), 2.80-3.07 (2H, m), 3.10 (3H, brs), 3.11-3.34 (1H, m), 3.31 (3H, s), 3.34 (3H, s), 3.40 (3H, s), 4.00-4.18 (1H, m), 4.29 (1H, d, J=7.5 Hz), 4.77 (2H, brs), 5.07 (1H, brs), 5.40-5.67 (1H, m), 5.80 (1H, t, J=10.5 Hz), 6.55 (1H, t, J=11.4 Hz), 6.91-7.24 (2H, m), 8.22 (1H, brs), 8.60 (1H, s).

Example 18

Compound 21

A Tebbe reagent-toluene solution (0.50 mol/L, 0.21 mL, 0.11 mmol) was added to a THF-toluene (3:1, 1.2 mL) solution of Herbimycin A (50 mg, 0.087 mmol) at −78° C. over a period of 10 minutes. After the temperature of the mixture was increased to −10° C. over a period of 2 hours, 28% aqueous ammonia (1.0 mL) was added thereto. The mixture was stirred at room temperature for 2 hours. Water was added to the mixture. Extraction was performed with ethyl acetate. The resulting organic layer was washed with a saturated saline solution and dried over anhydrous sodium sulfate. The solvent was distilled off under reduced pressure. The resulting residues were purified by thin-layer chromatography (chloroform/methanol=9/1) to yield Compound 21 (4.7 mg, 9%).

ESI Mass (m/z): 607.3 $(M+NH_4^+)^+$.

$^1$H-NMR: δ ppm (270 MHz, CDCl$_3$) 0.96 (3H, d, J=5.1 Hz), 1.06 (3H, d, J=6.6 Hz), 1.42-1.56 (1H, m), 1.58-1.90 (5H, m), 2.01 (3H, s), 2.63-2.81 (1H, m), 3.32 (3H, s), 3.35 (3H, s), 3.36 (3H, s), 3.41 (3H, s), 3.24-3.61 (5H, m), 3.52 (2H, s), 4.49 (1H, d, J=7.0 Hz), 4.56 (1H, s), 5.35 (2H, brs), 5.49 (1H, s), 5.84 (1H, dd, J=11.6, 7.6 Hz), 6.02 (1H, dd, J=1.9, 1.1 Hz), 6.52 (1H, t, J=10.5 Hz), 6.85 (1H, brs), 7.01 (1H, d, J=11.6 Hz), 7.09 (1H, s), 7.25-7.42 (1H, m).

Example 19

Compound 22

A trimethylsilylmethylmagnesium chloride-THF solution (1.0 mol/L, 0.87 mL, 0.87 mmol) was added to a THF (3.5 mL) solution of Herbimycin A (100 mg, 0.17 mmol) at −78° C. The temperature of the mixture was increased to room temperature over a period of 4 hours. Water was added to the mixture. Extraction was performed with ethyl acetate. The resulting organic layer was washed with a saturated saline solution and dried over anhydrous sodium sulfate. The solvent was distilled off under reduced pressure to obtain residues. The resulting residues were used for the subsequent reaction without purification.

A tributylammonium fluoride-THF solution (1.0 mol/L, 0.032 mL, 0.032 mmol) was added to a THF (0.20 mL) solution of the resulting residues (0.021 mmol) at 0° C. After the mixture was stirred at room temperature for 6 hours, water was added to the mixture. Extraction was performed with ethyl acetate. The resulting organic layer was washed with a saturated saline solution and dried over anhydrous sodium sulfate. The solvent was distilled off under reduced pressure. The resulting residues were purified by thin-layer chromatography (methanol/chloroform=1/9) to yield Compound 22 (3.6 mg, 29%, 2 steps).

ESI Mass (m/z): 591.3 $(M+H)^+$.

$^1$H-NMR: δ ppm (300 MHz, CDCl$_3$) 0.82-1.00 (1H, m), 0.89 (3H, d, J=6.9 Hz), 1.01-1.19 (3H, m), 1.20-1.42 (3H, m), 1.44-1.72 (2H, m), 1.76 (3H, s), 2.03 (3H, s), 2.24-2.46 (1H, m), 2.74-3.20 (5H, m), 3.29 (3H, s), 3.33 (3H, s), 3.38 (3H, s), 3.89-4.12 (1H, m), 4.31 (1H, d, J=8.7 Hz), 4.62 (2H, s), 4.51-4.90 (2H, m), 4.93-5.10 (1H, m), 5.44-5.58 (1H, m), 5.76 (1H, t, J=8.7 Hz), 6.54 (1H, t, J=11.4 Hz), 6.96-7.21 (1H, s), 8.21 (1H, s).

Example 20

Compound 23

Benzyl alcohol (0.015 mL, 0.15 mmol), triphenylphosphine (38 mg, 0.15 mmol), and 1,1'-azobis(N,N'-dimethylformamide) (25 mg, 0.15 mmol) were added to a THF (0.15 mL) solution of Compound 7 (50 mg, 0.072 mmol) obtained in Example 5. After the resulting mixture was stirred at room temperature for 48 hours, water was added to the mixture. Extraction was performed with ethyl acetate. The resulting organic layer was washed with a saturated saline solution and dried over anhydrous sodium sulfate. The solvent was distilled off under reduced pressure. The resulting residues were purified by thin-layer chromatography (methanol/chloroform=1/9) to yield Compound 23 (45 mg, 79%).

ESI Mass (m/z): 798.4 $(M+NH_4^+)^+$.

Example 21

Compound 24

Ammonium fluoride (18 mg, 0.49 mmol) was added to a methanol (4.5 mL) solution of Compound 23 (35 mg, 0.045 mmol) obtained in Example 20. The mixture was stirred at room temperature for 5 hours. The solvent was distilled off under reduced pressure. The resulting residues were purified by thin-layer chromatography (methanol/chloroform=1/15) to yield Compound 24 (15 mg, 49%).

ESI Mass (m/z): 684.3 $(M+NH_4^+)^+$.

$^1$H-NMR: δ ppm (300 MHz, CD$_3$OD) 0.50-0.68 (3H, m), 0.97 (3H, d, J=6.6 Hz), 1.12-1.32 (4H, m), 1.68-1.86 (1H, m), 1.72 (3H, s), 2.00-2.43 (2H, m), 2.81-2.95 (1H, m), 3.01-3.27 (8H, m), 3.34 (3H, m), 3.53 (3H, s), 3.80-3.99 (1H, m), 4.18 (1H, s), 4.53 (2H, brs), 4.70 (1H, d, J=10.5 Hz), 4.86 (1H, d, J=7.2 Hz), 4.94-5.25 (2H, m), 6.00-6.17 (1H, m), 6.26 (1H, t, J=10.8 Hz), 6.54-6.65 (2H, m), 7.31-7.41 (6H, m), 7.55 (1H, s).

Example 22

Compound 25

Phenethyl alcohol (0.017 mL, 0.15 mmol), triphenylphosphine (38 mg, 0.15 mmol), and a diethyl azocarboxylate-toluene solution (40 wt %, 0.066 mL, 0.15 mmol) were added to a THF (0.40 mL) solution of Compound 7 (50 mg, 0.072 mmol) obtained in Example 5. After the mixture was stirred at room temperature for 12 hours, the solvent was distilled off under reduced pressure. The resulting residues were purified by thin-layer chromatography (methanol/chloroform=1/15) to yield Compound 25 (37 mg, 64%).

ESI Mass (m/z): 812.4 $(M+NH_4^+)^+$.

Example 23

Compound 26

Ammonium fluoride (18 mg, 0.49 mmol) was added to a methanol (4.5 mL) solution of Compound 25 (37 mg, 0.046 mmol) obtained in Example 22. The mixture was stirred at room temperature for 5 hours. The solvent was distilled off under reduced pressure. The resulting residues were purified by thin-layer chromatography (methanol/chloroform=1/15) to yield Compound 26 (20 mg, 62%).

ESI Mass (m/z): 698.3 $(M+NH_4^+)^+$.

$^1$H-NMR: δ ppm (300 MHz, CD$_3$OD) 0.45 (3H, d, J=6.6 Hz), 0.50-0.70 (1H, m), 0.96 (3H, d, J=6.6 Hz), 1.12-1.38 (4H, m), 1.53-1.74 (1H, m), 1.92-2.11 (4H, m), 2.18-2.46 (1H, m), 2.82-3.05 (3H, m), 3.11 (1H, s), 3.16-3.40 (10H, m), 3.49 (3H, s), 3.65 (1H, q, J=8.1 Hz), 3.85-4.03 (2H, m), 4.03-4.16 (1H, m), 4.62 (1H, s), 4.74-4.96 (2H, m), 5.00-5.31 (2H, m), 6.05-6.23 (1H, m), 6.35 (1H, t, J=11.4 Hz), 6.45-6.59 (2H, m), 7.21-7.39 (5H, m).

Example 24

Compound 27

Methanol (0.015 mL, 0.36 mmol), triphenylphosphine (95 mg, 0.36 mmol), and a diethyl azocarboxylate-toluene solution (40 wt %, 0.17 mL, 0.36 mmol) were added to a THF (0.73 mL) solution of Compound 7 (100 mg, 0.15 mmol) obtained in Example 5. After the mixture was stirred at room temperature for 6.5 hours, the solvent was distilled off under reduced pressure. The resulting residues were purified by thin-layer chromatography (ethyl acetate/hexane=2/1) to yield Compound 27 (65 mg, 8%).

ESI Mass (m/z): 705.3 $(M+H)^+$.

Example 25

Compound 28

Ammonium fluoride (33 mg, 0.89 mmol) was added to a methanol (9 mL) solution of Compound 27 (65 mg, 0.090 mmol). The mixture was stirred at room temperature for 7 hours. The solvent was distilled off under reduced pressure. The resulting residues were purified by thin-layer chromatography (methanol/chloroform=1/15) to yield Compound 28 (49 mg, 93%).

ESI Mass (m/z): 608.2 $(M+NH_4^+)^+$.

$^1$H-NMR: δ ppm (300 MHz, CD$_3$OD) 0.63-0.80 (1H, m), 0.67 (3H, d, J=6.6 Hz), 0.96 (3H, d, J=6.3 Hz), 1.22 (3H, s), 1.61-1.77 (1H, m), 1.99 (3H, s), 2.13-2.41 (2H, m), 2.91-3.05 (1H, m), 3.11 (3H, s), 3.19-3.24 (1H, m), 3.26 (3H, s), 3.29-3.38 (3H, m), 3.34 (3H, s), 3.51 (3H, s), 3.54 (3H, s), 3.86-4.03 (1H, m), 4.46 (1H, d, J=4.5 Hz), 4.48-5.14 (2H, m), 5.16 (1H, d, J=10.8 Hz), 5.59-6.25 (1H, m), 6.35 (1H, t, J=11.4 Hz), 5.59-6.69 (2H, m), 7.84 (1H, d, J=7.5 Hz).

Example 26

Compound 29

3-dimethylaminopropanol (0.015 mL, 0.13 mmol), triphenylphosphine (34 mg, 0.13 mmol), and a diethyl azocarboxylate-toluene solution (40 wt %, 0.056 mL, 0.13 mmol) were added to a THF (0.43 mL) solution of Compound 7 (60 mg, 0.087 mmol) obtained in Example 5. After the mixture was stirred at room temperature for 49 hours, the solvent was distilled off under reduced pressure. The resulting residues were purified by thin-layer chromatography (methanol/chloroform=1/9) to yield Compound 29 (5.2 mg, 8%).

ESI Mass (m/z): 776.5 $(M+H)^+$.

Example 27

Compound 30

Ammonium fluoride (2.5 mg, 0.068 mmol) was added to a methanol (0.34 mL) solution of Compound 29 (5.2 mg, 0.0067 mmol) obtained in Example 26. After the mixture was stirred at room temperature for 1 hour, the solvent was distilled off under reduced pressure. The resulting residues were purified by thin-layer chromatography (methanol/chloroform=1/15) to yield Compound 30 (3.3 mg, 69%).

ESI Mass (m/z): 662.4 $(M+H)^+$.

$^1$H-NMR: δ ppm (270 MHz, CDCl$_3$) 0.83 (3H, d, J=6.8 Hz), 1.10 (1H, brd, J=14.6 Hz), 1.23 (3H, d, J=6.5 Hz), 1.21-1.34 (1H, m), 1.35-1.63 (2H, m), 1.79 (3H, d, J=1.4 Hz), 2.06 (3H, s), 2.17 (3H, s), 2.17 (3H, s), 2.58-2.76 (1H, m), 2.72 (3H, s), 2.77-2.87 (1H, m), 2.88-3.00 (1H, m), 3.21 (3H, s), 3.22 (3H, s), 3.39 (3H, s), 3.49 (1H, d, J=10.3 Hz), 3.96 (3H, s), 4.03 (1H, d, J=16.7 Hz), 4.57 (1H, d, J=9.2 Hz), 4.67 (2H, brs), 5.00 (1H, s), 5.10 (1H, d, J=17.0 Hz), 5.50 (1H, d, J=8.9 Hz), 5.86 (1H, t, J=11.1 Hz), 6.60 (1H, t, J=11.3 Hz), 6.83 (1H, dd, J=7.6, 1.5 Hz), 7.08 (1H, d, J=7.6 Hz), 7.18 (1H, d, J=13.2 Hz), 8.52 (1H, dd, J=8.4, 1.6 Hz), 9.78 (1H, s).

Example 28

Compound 31

Potassium carbonate (40 mg, 0.28 mmol) and (2-chloroethyl)dimethylamine hydrochloride (21 mg, 0.14 mmol) were added to an acetonitrile (7.2 mL) solution of Compound 7 (50 mg, 0.072 mmol) obtained in Example 5. The mixture was stirred at 40° C. for 3.5 hours. The solvent was distilled off under reduced pressure. The resulting residues were purified by thin-layer chromatography (ethyl acetate) to yield Compound 31 (43 mg, 78%). ESI Mass (m/z): 762.5 $(M+H)^+$.

Example 29

Compound 32

Ammonium fluoride (20 mg, 0.55 mmol) was added to a methanol (1.1 mL) solution of Compound 31 (42 mg, 0.055 mmol) obtained in Example 28. The mixture was stirred at room temperature for 40 minutes. The solvent was distilled off under reduced pressure. The resulting residues were purified by thin-layer chromatography (methanol/chloroform=1/9) to yield Compound 32 (33 mg, 93%).

ESI Mass (m/z): 648.4 $(M+H)^+$.

$^1$H-NMR: δ ppm (270 MHz, CDCl$_3$) 0.91 (3H, d, J=6.6 Hz), 1.00 (3H, d, J=7.2 Hz), 1.21-1.40 (1H, m), 1.50-1.84 (2H, m), 1.67 (3H, s), 2.10 (3H, s), 2.14 (6H, s), 2.26-2.44 (1H, m), 2.70-2.94 (2H, m), 3.24 (3H, s), 3.25-3.48 (3H, m), 3.32 (3H, s), 3.33 (3H, s), 3.34 (3H, s), 3.50-3.64 (1H, m), 4.29 (1H, d, J=6.6 Hz), 4.41 (2H, d, J=4.8 Hz), 4.80 (2H, brs), 5.13 (1H, s), 5.44 (1H, d, J=9.3 Hz), 5.54-5.82 (1H, m), 6.50 (1H, t, J=11.4 Hz), 6.65 (1H, d, J=2.7 Hz), 6.70-6.96 (1H, m), 8.18 (1H, brs), 10.98 (1H, brs).

Example 30

Compound 33

Potassium carbonate (16 mg, 0.12 mmol) and (2-chloroethyl)diethylamine hydrochloride (10 mg, 0.058 mmol) were added to an acetonitrile (2.9 mL) solution of Compound 7 (20 mg, 0.029 mmol) obtained in Example 5. The mixture was stirred at 40° C. for 2.5 hours. The solvent was distilled off under reduced pressure. The resulting residues were purified by thin-layer chromatography (ethyl acetate) to yield Compound 33 (22 mg, 95%). ESI Mass (m/z): 790.5 $(M+H)^+$.

Example 31

Compound 34

Ammonium fluoride (12 mg, 0.32 mmol) was added to a methanol (0.55 mL) solution of Compound 33 (22 mg, 0.028 mmol) obtained in Example 30. The mixture was stirred at room temperature for 1 hour. The solvent was distilled off under reduced pressure. The resulting residues were purified by thin-layer chromatography (methanol/chloroform 1/9) to yield Compound 34 (13.5 mg, 73%).

ESI Mass (m/z): 676.4 $(M+H)^+$.

$^1$H-NMR: δ ppm (300 MHz, CDCl$_3$) 0.83 (3H, d, J=4.8 Hz), 0.93 (6H, t, J=6.9 Hz), 1.00 (3H, d, J=6.9 Hz), 1.12-1.36 (2H, m), 1.47-1.74 (4H, m), 1.74-1.96 (1H, m), 2.07 (3H, s), 2.56 (4H, q, J=6.9 Hz), 2.57-2.88 (3H, m), 3.20 (3H, s), 3.32

(3H, s), 3.34 (3H, s), 3.37 (3H, s), 3.24-3.43 (3H, m), 3.63-3.78 (1H, m), 4.06-4.40 (2H, m), 4.48 (1H, d, J=4.2 Hz), 4.75 (1H, brs), 5.12 (1H, s), 5.37 (1H, d, J=9.0 Hz), 5.46-5.75 (1H, m), 6.43 (1H, t, J=11.4 Hz), 6.51-6.99 (1H, m), 6.67 (1H, d, J=3.0 Hz), 7.90 (1H, brs).

Example 32

Compound 35

Potassium carbonate (16 mg, 0.12 mmol) and 1-(2-chloroethyl)pyrrolidine hydrochloride (11 mg, 0.058 mmol) were added to an acetonitrile (2.9 mL) solution of Compound 7 (20 mg, 0.029 mmol) obtained in Example 5. The mixture was stirred at 40° C. for 4.5 hours. The solvent was distilled off under reduced pressure. The resulting residues were purified by thin-layer chromatography (ethyl acetate) to yield Compound 35 (22 mg, 96%). ESI Mass (m/z): 788.5 (M+H)$^+$.

Example 33

Compound 36

Ammonium fluoride (11 mg, 0.30 mmol) was added to a methanol (0.56 mL) solution of Compound 35 (22 mg, 0.028 mmol) obtained in Example 32. The mixture was stirred at room temperature for 40 minutes. The solvent was distilled off under reduced pressure. The resulting residues were purified by thin-layer chromatography (methanol/chloroform=1/9) to yield Compound 36 (15 mg, 78%).
ESI Mass (m/z): 674.4 (M+H)$^+$.
$^1$H-NMR: δ ppm (270 MHz, CDCl$_3$) 0.85 (3H, d, J=3.9 Hz), 1.03 (3H, d, J=7.2 Hz), 1.12-1.48 (2H, m), 1.50-1.86 (9H, m), 2.08 (3H, s), 2.30-2.66 (5H, m), 2.71-2.93 (1H, m), 2.93-3.13 (1H, m), 3.23 (3H, s), 3.25-3.50 (11H, m), 3.54-3.70 (1H, m), 4.30 (1H, d, J=6.6 Hz), 4.31-4.54 (2H, m), 4.77 (2H, brs), 5.17 (1H, s), 5.43 (1H, d, J=9.0 Hz), 5.51-5.57 (1H, m), 6.48 (1H, t, J=11.4 Hz), 6.66 (1H, d, J=3.3 Hz), 6.74-7.01 (1H, m), 8.14 (1H, brs), 10.66 (1H, brs).

Example 34

Compound 37

Potassium carbonate (16 mg, 0.12 mmol) and 1-(2-chloroethyl)morpholine hydrochloride (11 mg, 0.058 mmol) were added to an acetone (2.9 mL) solution of Compound 7 (20 mg, 0.029 mmol) obtained in Example 5. The mixture was stirred at 40° C. for 9 hours. The solvent was distilled off under reduced pressure. The resulting residues were purified by thin-layer chromatography (ethyl acetate) to yield Compound 37 (8.4 mg, 36%).
ESI Mass (m/z): 804.5 (M+H)$^+$.

Example 35

Compound 38

Ammonium fluoride (3.7 mg, 0.10 mmol) was added to a methanol (1 mL) solution of Compound 37 (8.4 mg, 0.010 mmol) obtained in Example 34. The mixture was stirred at room temperature for 1 hour. The solvent was distilled off under reduced pressure. The resulting residues were purified by thin-layer chromatography (methanol/chloroform=1/9) to yield Compound 38 (5.0 mg, 71%).
ESI Mass (m/z): 690.4 (M+H)$^+$.
$^1$H-NMR: δ ppm (270 MHz, CDCl$_3$) 0.83 (3H, d, J=5.7 Hz), 1.03 (3H, d, J=7.0 Hz), 1.41-1.92 (6H, m), 2.11 (3H, s), 2.26-2.93 (7H, m), 3.05-3.47 (3H, m), 3.23 (3H, s), 3.33 (3H, s), 3.34 (3H, s), 3.36 (3H, s), 3.50-3.81 (5H, m), 4.10-4.71 (3H, m), 4.72 (2H, brs), 5.15 (1H, s), 5.36 (1H, d, J=8.9 Hz), 5.51-5.88 (1H, m), 6.47 (1H, t, J=11.6 Hz), 6.67 (1H, d, J=3.0 Hz), 6.71-6.90 (1H, m), 6.87 (1H, brs), 7.93 (1 h, brs).

Example 36

Compound 39

To a THF (0.15 mL) solution of Compound 7 (50 mg, 0.072 mmol) obtained in Example 5, 4-hydroxy-4H-pyran (0.014 mL, 0.15 mmol), triphenylphosphine (38 mg, 0.15 mmol), and 1,1'-azobis(N,N'-dimethylformamide) (25 mg, 0.15 mmol) were added. After the mixture was stirred at room temperature for 6 days, water was added to the mixture. Extraction was performed with ethyl acetate. The resulting organic layer was washed with a saturated saline solution and dried over anhydrous sodium sulfate. The solvent was distilled off under reduced pressure. The resulting residues were purified by thin-layer chromatography (methanol/chloroform=1/9) to yield Compound 39 (15 mg, 27%).
ESI Mass (m/z): 775.5 (M+H)$^+$.

Example 37

Compound 40

Ammonium fluoride (7.0 mg, 0.18 mmol) was added to a methanol (0.40 mL) solution of Compound 39 (15 mg, 0.019 mmol) obtained in Example 36. The mixture was stirred at room temperature for 50 minutes. The solvent was distilled off under reduced pressure. The resulting residues were purified by thin-layer chromatography (methanol/chloroform=1/9) to yield Compound 40 (9.5 mg, 76%).
ESI Mass (m/z): 661.4 (M+H)$^+$.
$^1$H-NMR: δ ppm (300 MHz, CDCl$_3$) 0.50 (3H, d, J=5.7 Hz), 0.97 (3H, d, J=6.6 Hz), 1.10-1.38 (2H, m), 1.22 (3H, s), 1.59-1.99 (4H, m), 2.01 (3H, s), 2.12-2.47 (2H, m), 2.78-2.95 (1H, m), 3.10 (3H, s), 3.15-3.26 (1H, m), 3.26-3.33 (1H, m), 3.30 (3H, s), 3.33 (3H, s), 3.33-3.41 (2H, m), 3.55 (3H, s), 3.67-3.78 (2H, m), 3.78-4.04 (4H, m), 4.57 (1H, s), 4.87 (1H, d, J=9.3 Hz), 5.05 (1H, t, J=10.2 Hz), 5.15 (1H, d, J=10.5 Hz), 5.23 (1H, s), 6.04 (1H, d, J=11.1 Hz), 6.27 (1H, t, J=11.1 Hz), 6.54 (1H, brs), 6.58 (1H, d, J=3.0 Hz).

Example 38

Compound 41

Methyl glycolate (0.0060 mL, 0.071 mmol), triphenylphosphine (19 mg, 0.071 mmol), and 1,1'-azobis(N,N'-dimethylformamide) (13 mg, 0.071 mmol) were added to a 1,2-dichloroethane (0.18 mL) solution of Compound 2 (20 mg, 0.036 mmol) obtained in Example 1. The mixture was stirred at room temperature for 3.5 hours. The solvent was distilled off under reduced pressure. The resulting residues were purified by thin-layer chromatography (methanol/chloroform=1/9) to yield Compound 41 (4.7 mg, 21%).
ESI Mass (m/z): 633.3 (M+H)$^+$.
$^1$H-NMR: δ ppm (270 MHz, CDCl$_3$) 0.81-1.01 (3H, m), 1.14-1.15 (4H, m), 1.77 (3H, s), 2.02 (3H, s), 2.22-2.40 (4H, m), 2.40-2.66 (2H, m), 2.67-2.88 (3H, m), 2.89-3.12 (1H, m), 3.00 (3H, s), 3.16 (3H, s), 3.17-3.50 (8H, m), 3.70-3.87 (1H, m), 3.96-4.20 (1H, m), 4.36 (1H, d, J=9.2 Hz), 4.57 (2H, brs), 5.39 (1H, d, J=8.1 Hz), 5.82 (1H, t, J=10.5 Hz), 6.41 (1H, d, J=2.7 Hz), 6.64 (1H, t, J=11.1 Hz), 6.91 (1H, d, J=11.3 Hz), 7.89 (1H, brs).

Example 39

Compound 42

Pd/C (20 wt %, 50 mg) was added to an ethanol (10 mL) solution of Herbimycin A (250 mg, 0.44 mmol). The mixture was stirred for 5.5 hours in a hydrogen atmosphere. Insoluble matter was filtered off with cerite. Water was added to the resulting filtrate. Extraction was performed with chloroform. The resulting organic layer was dried over anhydrous sodium sulfate. The solvent was distilled off under reduced pressure. The resulting residues were purified by thin-layer chromatography (methanol/chloroform=1/15) to yield Compound 42 (230 mg, 91%).

ESI Mass (m/z): 598.2 $(M+NH_4^+)^+$.

$^1$H-NMR: δ ppm (300 MHz, CDCl$_3$) 0.79-1.11 (7H, m), 1.21-1.33 (6H, m), 1.33-1.72 (5H, m), 1.72-1.93 (2H, m), 2.20-2.61 (2H, m), 2.61-2.89 (2H, m), 3.06-3.59 (16H, m), 4.68 (2H, brs), 5.05 (1H, d, J=5.7 Hz), 5.26-5.62 (1H, m), 6.11-6.50 (1H, m), 7.80-8.48 (3H, m).

Compounds shown in Table 3 below were prepared by methods described in reference examples below. These compounds exhibited Hsp90 protein-binding activity in Hsp90 protein binding assay described in Test Example 1.

TABLE 3

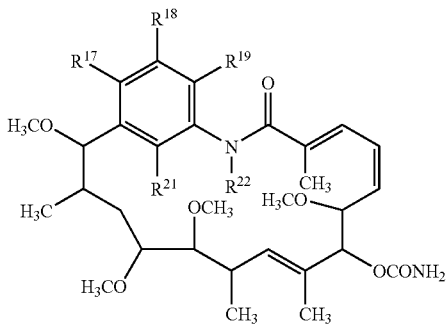

| Reference Example No. | Compound No. | $R^{17}$ | $R^{18}$ | $R^{19}$ | $R^{21}$ | $R^{22}$ |
|---|---|---|---|---|---|---|
| 1 | 1 | H | OH | H | OH | H |
| 2 | 3 | H | OCOCH$_3$ | H | OH | COCH$_3$ |
| 3 | 17 | H | OH | H | OH | CH$_3$ |

Reference Example 1

Compound 1

An aqueous 10% sodium dithionite solution (13.9 mL, 8.00 mmol) was added dropwise to an ethyl acetate (19 mL) solution of Herbimycin A (200 mg, 0.348 mmol). The mixture was stirred at room temperature for 15 minutes and was then subjected to extraction with ethyl acetate. The resulting organic layer was washed with a saturated saline solution and dried over anhydrous sodium sulfate. The solvent was distilled off under reduced pressure. The resulting residues were crystallized in chloroform-hexane (1:8) to obtain Compound 1 (202 mg, 98%).

ESI Mass (m/z): 577 (M+1)$^+$.

$^1$H-NMR: δ ppm (300 MHz, CDCl$_3$) 0.84-0.96 (6H, m), 1.00-1.21 (1H, m), 1.21-1.37 (2H, m), 1.76 (3H, s), 2.06 (3H, s), 2.16-2.54 (1H, m), 2.73-3.21 (4H, m), 3.21-3.46 (11H, m), 3.64-4.11 (1H, m), 4.17-4.40 (1H, m), 4.50-5.32 (3H, m), 5.37-5.68 (1H, m), 5.68-5.90 (1H, m), 6.33 (1H, s), 6.55 (1H, t, J=11.4 Hz), 6.81-7.19 (1H, m), 7.19-7.92 (1H, m), 8.12 (1H, s), 8.40 (1H, brs).

Reference Example 2

Compound 3

Compound 3 was obtained simultaneously with Compound 4 in Example 2.

ESI Mass (m/z): Compound 3 678 $(M+NH_4^+)^+$.

Reference Example 3

Compound 17

Silver oxide (15 mg, 0.063 mmol) and methyl iodide (64 μL, 1.1 mmol) were added to an acetonitrile (1.0 mL) solution of Herbimycin A (30 mg, 0.052 mmol). The mixture was stirred for 18 hours in the dark. Insoluble matter was filtered off with cerite. The solvent was distilled off under reduced pressure. The resulting residues were purified by thin-layer chromatography (methanol/chloroform=1/15) to yield Compound 53 (32 mg, 98%).

An aqueous 10% sodium dithionite solution (2.0 mL, 0.12 mmol) was added to an ethyl acetate (3.3 mL) solution of Compound 53 (32 mg, 0.052 mmol). The mixture was stirred at room temperature for 1.5 hours. The mixture was subjected to extraction with ethyl acetate. The resulting organic layer was washed with a saturated saline solution and dried over anhydrous sodium sulfate. The solvent was distilled off under reduced pressure. The resulting residues were purified by thin-layer chromatography (methanol/chloroform=1/15) to yield Compound 17 (13 mg, 37%).

ESI Mass (m/z): 589.2 (M+H)$^+$.

Compound 53

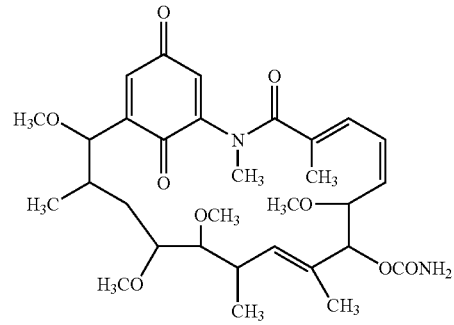

INDUSTRIAL APPLICABILITY

The present invention provides a benzenoid ansamycin derivative or a pharmaceutically acceptable salt thereof useful as an Hsp90 family protein inhibitor.

The invention claimed is:
1. A compound represented by Formula (I)

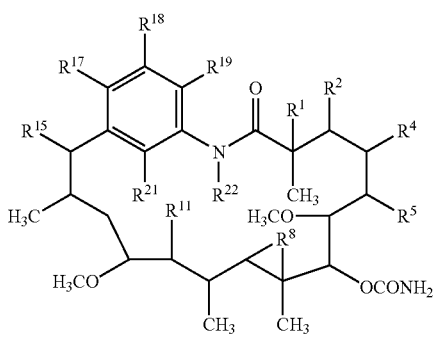

{wherein $R^1$ and $R^2$ each represent a hydrogen atom or are combined together to form a bond,
$R^8$ represents a bond or an oxygen atom,
$R^{11}$ represents hydroxy, substituted or unsubstituted lower alkoxy or substituted or unsubstituted lower alkanoyloxy,
$R^{15}$ represents a hydrogen atom or methoxy,
$R^{22}$ represents a hydrogen atom, substituted or unsubstituted lower alkyl, substituted or unsubstituted lower alkanoyl or substituted or unsubstituted aroyl,
$R^4$ and $R^5$ each represent a hydrogen atom or are combined together to form a bond, and
(i) when $R^4$ and $R^5$ represent hydrogen atoms; then
(a) $R^{18}$ represents a hydrogen atom, hydroxy, cyano, substituted or unsubstituted lower alkyl, substituted or unsubstituted cycloalkyl, substituted or unsubstituted aryl, substituted or unsubstituted aralkyl, substituted or unsubstituted lower alkoxy, substituted or unsubstituted cycloalkyloxy, substituted or unsubstituted aralkyloxy, substituted or unsubstituted heteroalicyclic-oxy, substituted or unsubstituted aryloxy, substituted or unsubstituted heteroaryloxy, substituted or unsubstituted lower alkanoyloxy, substituted or unsubstituted aroyloxy, substituted or unsubstituted lower alkylsulfonyloxy, substituted or unsubstituted arylsulfonyloxy or —$OSiR^{30}R^{31}R^{32}$ (wherein $R^{30}$, $R^{31}$ and $R^{32}$ may be the same or different and each represents lower alkyl or aryl),
(b) $R^{21}$ represents hydroxy, substituted or unsubstituted lower alkoxy, substituted or unsubstituted cycloalkyloxy, substituted or unsubstituted aralkyloxy, substituted or unsubstituted heteroalicyclic-oxy, substituted or unsubstituted aryloxy, substituted or unsubstituted heteroaryloxy, substituted or unsubstituted lower alkanoyloxy, substituted or unsubstituted aroyloxy, substituted or unsubstituted lower alkylsulfonyloxy or substituted or unsubstituted arylsulfonyloxy, and
(c) $R^{17}$ and $R^{19}$ may be the same or different and each represents a hydrogen atom, hydroxy, halogen, substituted or unsubstituted lower alkylsulfanyl, substituted or unsubstituted lower alkylsulfinyl, substituted or unsubstituted lower alkyl, substituted or unsubstituted cycloalkyl, substituted or unsubstituted aryl or substituted or unsubstituted heteroaryl, and
(ii) when $R^4$ and $R^5$ are combined together to form a bond, then
(a) $R^{18}$ represents a hydrogen atom, hydroxy, cyano, substituted or unsubstituted lower alkyl, substituted or unsubstituted cycloalkyl, substituted or unsubstituted aryl, substituted or unsubstituted aralkyl, substituted or unsubstituted lower alkoxy, substituted or unsubstituted cycloalkyloxy, substituted or unsubstituted aryloxy, substituted or unsubstituted aralkyloxy, substituted or unsubstituted heteroalicyclic-oxy, substituted or unsubstituted heteroaryloxy, substituted or unsubstituted lower alkanoyloxy, substituted or unsubstituted aroyloxy, substituted or unsubstituted lower alkylsulfonyloxy, substituted or unsubstituted arylsulfonyloxy, or —$OSiR^{30}R^{31}R^{32}$,
(b) $R^{21}$ represents a hydrogen atom, hydroxy, substituted or unsubstituted lower alkoxy, substituted or unsubstituted cycloalkyloxy, substituted or unsubstituted aryloxy, substituted or unsubstituted aralkyloxy, substituted or unsubstituted heteroalicyclic-oxy, substituted or unsubstituted heteroaryloxy, substituted or unsubstituted lower alkanoyloxy, substituted or unsubstituted aroyloxy, substituted or unsubstituted lower alkylsulfonyloxy or substituted or unsubstituted arylsulfonyloxy, and
(c) with the further provisos (1)-(3)
(1) when $R^{18}$ is hydroxy, lower alkoxy or lower alkanoyloxy, and $R^{21}$ is a hydrogen atom, hydroxy or lower alkoxy,
then $R^{17}$ and $R^{19}$ may be the same or different and each represents a hydrogen atom, halogen, substituted or unsubstituted cycloalkyloxy, substituted or unsubstituted lower alkylsulfanyl, substituted or unsubstituted lower alkylsulfinyl, substituted or unsubstituted lower alkyl, substituted or unsubstituted cycloalkyl, substituted or unsubstituted aryl or substituted or unsubstituted heteroaryl (with the proviso that $R^{17}$ and $R^{19}$ are not simultaneously hydrogen atoms),
(2) when $R^{18}$ is hydroxy, lower alkoxy or lower alkanoyloxy, and $R^{21}$ is substituted lower alkoxy, substituted or unsubstituted cycloalkyloxy, substituted or unsubstituted aryloxy, substituted or unsubstituted aralkyloxy, substituted or unsubstituted heteroalicyclic-oxy, substituted or unsubstituted heteroaryloxy, substituted or unsubstituted lower alkanoyloxy, substituted or unsubstituted aroyloxy, substituted or unsubstituted lower alkylsulfonyloxy or substituted or unsubstituted arylsulfonyloxy,
then $R^{17}$ and $R^{19}$ may be the same or different and each represents a hydrogen atom, hydroxy, halogen, substituted or unsubstituted lower alkoxy, substituted or unsubstituted cycloalkyloxy, substituted or unsubstituted lower alkylsulfanyl, substituted or unsubstituted lower alkylsulfinyl, —$NR^{40}R^{41}$ (wherein $R^{40}$ and $R^{41}$ may be the same or different and each represents a hydrogen atom, substituted or unsubstituted lower alkyl, substituted or unsubstituted cycloalkyl, substituted or unsubstituted lower alkenyl, substituted or unsubstituted lower alkynyl, substituted or unsubstituted aryl, substituted or unsubstituted heteroaryl, or $R^{40}$ and $R^{41}$ are combined together with the adjacent nitrogen atom thereto to form a substituted or unsubstituted nitrogen-containing heterocyclic group), substituted or unsubstituted lower alkyl, substituted or unsubstituted cycloalkyl, substituted or unsubstituted aryl or substituted or unsubstituted heteroaryl, and
(3) when $R^{18}$ is a hydrogen atom, cyano, substituted or unsubstituted lower alkyl, substituted or unsubstituted cycloalkyl, substituted or unsubstituted aryl, substituted or unsubstituted aralkyl, substituted lower alkoxy, substituted or unsubstituted cycloalkyloxy, substituted or unsubstituted aryloxy, substituted or unsubstituted aralkyloxy, substituted or unsubstituted heteroalicyclic-oxy, substituted or unsubstituted heteroaryloxy, substituted lower alkanoyloxy, substituted or unsubstituted aroyloxy, substituted or unsubstituted lower alkylsulfonyloxy, substituted or unsubstituted arylsulfonyloxy or —OSiR$^{30}$R$^{31}$R$^{32}$, then R$^{17}$ and R$^{19}$ may be the same or different and each represents a hydrogen atom, hydroxy, halogen, substituted or unsubstituted lower alkoxy, substituted or unsubstituted cycloalkyloxy, substituted or unsubstituted lower alkylsulfanyl, substituted or unsubstituted lower alkylsulfinyl, —NR$^{40}$R$^{41}$, substituted or unsubstituted lower alkyl, substituted or unsubstituted cycloalkyl, substituted or unsubstituted aryl or substituted or unsubstituted heteroaryl, and each of the substituted lower alkyl, substituted lower alkoxy, substituted lower alkanoyl, substituted lower alkanoyloxy, substituted lower alkylsulfanyl, substituted lower alkylsulfinyl, substituted cycloalkyl, substituted cycloalkyloxy, substituted lower alkylsulfonyloxy, substituted lower alkenyl, and substituted lower alkynyl has 1 to 3 substituents, wherein the substituents may be the same or different and the substituents are selected from the group consisting of halogen, hydroxy, cyano, carboxy, sulfanyl, amino, lower alkoxy optionally substituted by Substituent A (wherein the Substituent A represents one to three substituents selected from the group consisting of halogen, hydroxy, lower alkoxy, amino, lower alkylamino, di(lower alkyl)amino, nitro, and sulfanyl), lower alkylsulfanyl optionally substituted by Substituent A, lower alkylamino optionally substituted by Substituent A, di(lower alkyl)amino optionally substituted by Substituent A, aralkylamino optionally substituted by Substituent A, lower alkoxycarbonylamino optionally substituted by Substituent A, lower alkanoylamino optionally substituted by Substituent A, aroylamino optionally substituted by Substituent A, a heteroalicyclic group optionally substituted by Substituent A, heteroaryl optionally substituted by Substituent A, aryl optionally substituted by Substituent A, lower alkoxycarbonyl optionally substituted by Substituent A, lower alkanoyloxy optionally substituted by Substituent A, and tri (lower alkyl) silyl, each of the substituted aryl, substituted aryloxy, substituted aroyl, substituted aroyloxy, substituted arylsulfonyloxy, substituted aralkyl, substituted aralkyloxy, substituted heteroaryl, substituted heteroaryloxy, substituted heteroalicyclic-oxy, and a substituted nitrogen-containing heterocyclic group formed together with the adjacent nitrogen atom has 1 to 3 substituents, wherein the substituents may be the same or different and the substituents are selected from the group consisting of halogen, hydroxy, cyano, carboxy, sulfanyl, amino, lower alkoxy optionally substituted by Substituent A, lower alkylsulfanyl optionally substituted by Substituent A, lower alkylamino optionally substituted by Substituent A, di(lower alkyl)amino optionally substituted by Substituent A, aralkylamino optionally substituted by Substituent A, lower alkoxycarbonylamino optionally substituted by Substituent A, lower alkanoylamino optionally substituted by Substituent A, aroylamino optionally substituted by Substituent A, a heteroalicyclic group optionally substituted by Substituent A, heteroaryl optionally substituted by Substituent A, aryl optionally substituted by Substituent A, lower alkoxycarbonyl optionally substituted by Substituent A, lower alkanoyloxy optionally substituted by Substituent A, lower alkyl optionally substituted by Substituent A, lower alkanoyl optionally substituted by Substituent A, and aroyl optionally substituted by Substituent A, the heteroaryl and the heteroaryl moiety in the heteroaryloxy represent furyl, thienyl, pyroryl, imidazolyl, pyrazolyl, oxazolyl, isoxazolyl, oxadiazolyl, thiazolyl, isothiazolyl, thiadiazolyl, triazolyl, tetrazolyl, pyridyl, pyridazinyl, pyrimidinyl, pyrazinyl, traizinyl, benzofuranyl, benzothiophenyl, benzoxazolyl, benzothiazolyl, isoindolyl, indolyl, indazolyl, benzoimidazolyl, benzotriazolyl, oxazolopyrimidinyl, thiazolopyrimidinyl, pyrrolopyridinyl, pyrrolopyrimidinyl, imidazopyridinyl, purinyl, quinolinyl, isoquinolinyl, cinnolinyl, phthalazinyl, quinazolinyl, quinoxalinyl, or naphthylidinyl, the heteroalicyclic moiety in the heteroalicyclic-oxy represents aziridinyl, azetidinyl, pyrrolidinyl, piperidino, piperidinyl, azepanyl, 1,2,5,6-tetrahydropyridyl, imidazolidinyl, pyrazolidinyl, piperazinyl, homopiperazinyl, pyrazolinyl, oxiranyl, tetrahydrofuranyl, tetrahydro-2H-pyranyl, 5,6-dihydro-2H-pyranyl, oxazolidinyl, morpholino, morpholinyl, thioxazolidinyl, thiomorpholinyl, 2H-oxazolyl, 2H-thioxazolyl, dihydroindolyl, dihydroisoindolyl, dihydrobenzofuranyl, benzoimidazolidinyl, dihydrobenzooxazolyl, dihydrobenzothioxazolyl, benzodioxolinyl, tetrahydroquinolyl, tetrahydroisoquinolyl, dihydro-2H-chromanyl, dihydro-1H-chromanyl, dihydro-2H-thiochromanyl, dihydro-1H-thiochromanyl, tetrahydroquinoxalinyl, tetrahydroquinazolinyl, or dihydrobenzodioxanyl, the nitrogen-containing heterocyclic group formed together with the adjacent nitrogen atom represents aziridinyl, azetidinyl, pyrrolidinyl, piperidino, azepanyl, pyroryl, imidazolidinyl, imidazolyl, pyrazolidinyl, pyrazolinyl, pyrazolyl, piperazinyl, homopiperazinyl, oxazolidinyl, 2H-oxazolyl, thioxazolidinyl, 2H-thioxazolyl, morpholino, thiomorpholinyl, dihydroindolyl, dihydroisoindolyl, indolyl, isoindolyl, tetrahydroquinolyl, tetrahydroisoquinolyl, dihydrobenzooxazolyl, dihydrobenzothioxazolyl, benzoimidazolidinyl, benzoimidazolyl, dihydroindazolyl, indazolyl, benzotriazolyl, pyrrolopyridinyl, pyrrolopyrimidinyl, imidazopyridinyl, or purinyl} or a pharmaceutically acceptable salt thereof.

2. The compound or the pharmaceutically acceptable salt thereof according to claim 1, wherein R$^1$, R$^2$, R$^4$ and R$^5$ are hydrogen atoms.

3. The compound or the pharmaceutically acceptable salt thereof according to claim 1, wherein R$^1$ and R$^2$ are combined together to form a bond.

4. The compound or the pharmaceutically acceptable salt thereof according to claim 1, wherein R$^1$ and R$^2$, and R$^4$ and R$^5$ are combined together to form bonds.

5. The compound or the pharmaceutically acceptable salt thereof according to any of claims 1 to 4, wherein R$^{18}$ is hydroxy, lower alkoxy or lower alkanoyloxy.

6. The compound or the pharmaceutically acceptable salt thereof according to claim 5, wherein R$^{21}$ is substituted or unsubstituted lower alkoxy, substituted or unsubstituted cycloalkyloxy, substituted or unsubstituted aryloxy, substituted or unsubstituted aralkyloxy, substituted or unsubstituted heteroalicyclic-oxy, substituted or unsubstituted heteroaryloxy, substituted or unsubstituted lower alkanoyloxy, substituted or unsubstituted aroyloxy, substituted or unsubstituted lower alkylsulfonyloxy or substituted or unsubstituted arylsulfonyloxy.

7. The compound or the pharmaceutically acceptable salt thereof according to claim 5, wherein $R^{21}$ is substituted or unsubstituted lower alkoxy, substituted or unsubstituted aralkyloxy or substituted or unsubstituted heteroalicyclic-oxy.

8. The compound or the pharmaceutically acceptable salt thereof according to any of claims 1 to 4, wherein $R^{18}$ is a hydrogen atom, cyano, substituted or unsubstituted lower alkyl, substituted or unsubstituted cycloalkyl, substituted or unsubstituted aryl, substituted or unsubstituted aralkyl, substituted lower alkoxy, substituted or unsubstituted cycloalkyloxy, substituted or unsubstituted aryloxy, substituted or unsubstituted aralkyloxy, substituted or unsubstituted heteroalicyclic-oxy, substituted or unsubstituted heteroaryloxy, substituted lower alkanoyloxy, substituted or unsubstituted aroyloxy, substituted or unsubstituted lower alkylsulfonyloxy, substituted or unsubstituted arylsulfonyloxy or —$OSiR^{30}R^{31}R^{32}$.

9. The compound or the pharmaceutically acceptable salt thereof according to any of claims 1 to 4, wherein $R^{18}$ is a hydrogen atom, cyano, substituted or unsubstituted lower alkyl, substituted or unsubstituted aroyloxy or —$OSiR^{30}R^{31}R^{32}$.

10. The compound or the pharmaceutically acceptable salt thereof according to any of claims 1 to 4, wherein $R^{18}$ is a hydrogen atom, cyano or substituted or unsubstituted lower alkyl.

11. The compound or the pharmaceutically acceptable salt thereof according to claim 8, wherein $R^{21}$ is hydroxy, substituted or unsubstituted lower alkoxy, substituted or unsubstituted aralkyloxy, substituted or unsubstituted heteroalicyclic-oxy, substituted or unsubstituted lower alkanoyloxy or substituted or unsubstituted lower alkylsulfonyloxy.

12. The compound or the pharmaceutically acceptable salt thereof according to claim 9, wherein $R^{21}$ is hydroxy, substituted or unsubstituted lower alkoxy, substituted or unsubstituted aralkyloxy or substituted or unsubstituted heteroalicyclic-oxy.

13. The compound or the pharmaceutically acceptable salt thereof according to claim 10, wherein $R^{21}$ is hydroxy.

14. The compound or the pharmaceutically acceptable salt thereof according to claim 11, wherein $R^{17}$ and $R^{19}$ may be the same or different and each is a hydrogen atom, halogen, substituted or unsubstituted lower alkylsulfanyl or substituted or unsubstituted lower alkylsulfinyl.

15. The compound or the pharmaceutically acceptable salt thereof according to claim 14, wherein $R^8$ represents a bond.

16. The compound or the pharmaceutically acceptable salt thereof according to claim 15, wherein $R^{11}$ is hydroxy or lower alkoxy.

17. The compound or the pharmaceutically acceptable salt thereof according to claim 15, wherein $R^{11}$ is methoxy.

18. The compound or the pharmaceutically acceptable salt thereof according to claim 16, wherein $R^{15}$ is methoxy.

19. A pharmaceutical composition which comprises, as an active ingredient, the compound or the pharmaceutically acceptable salt thereof described in claim 11.

20. A method for treating human chronic myelocytic leukemia, which comprises administering, to a patient in need thereof, an effective amount of the compound or the pharmaceutically acceptable salt thereof described in claim 1.

* * * * *